(12) United States Patent
Mark

(10) Patent No.: US 8,172,770 B2
(45) Date of Patent: May 8, 2012

(54) SYSTEM AND METHOD FOR MINIMALLY INVASIVE DISEASE THERAPY

(75) Inventor: Joseph L. Mark, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 19 days.

(21) Appl. No.: 11/550,209

(22) Filed: Oct. 17, 2006

(65) Prior Publication Data

US 2007/0123815 A1    May 31, 2007

Related U.S. Application Data

(63) Continuation-in-part of application No. 11/237,110, filed on Sep. 28, 2005.

(51) Int. Cl.
*A61B 1/00* (2006.01)
*A61B 6/00* (2006.01)
*A61B 10/00* (2006.01)
(52) U.S. Cl. ......... 600/562; 600/104; 600/431; 600/564
(58) Field of Classification Search .................. 600/104, 600/562, 431, 563, 564
See application file for complete search history.

(56) References Cited

U.S. PATENT DOCUMENTS

| 4,649,151 | A |   | 3/1987  | Dougherty et al. |          |
|-----------|---|---|---------|------------------|----------|
| 5,199,441 | A |   | 4/1993  | Hogle            |          |
| 5,261,889 | A | * | 11/1993 | Laine et al.     | 604/164.11 |
| 5,279,542 | A |   | 1/1994  | Wilk             |          |
| 5,817,048 | A |   | 10/1998 | Lawandy          |          |
| 5,913,813 | A |   | 6/1999  | Williams et al.  |          |
| 6,142,955 | A |   | 11/2000 | Farascioni et al.|          |
| 6,296,608 | B1| * | 10/2001 | Daniels et al.   | 600/104  |
| 6,315,737 | B1|   | 11/2001 | Skinner          |          |
| 6,371,904 | B1| * | 4/2002  | Sirimanne et al. | 600/3    |
| 6,413,204 | B1|   | 7/2002  | Winkler et al.   |          |
| 6,440,138 | B1|   | 8/2002  | Reiley et al.    |          |
| 6,482,142 | B1|   | 11/2002 | Winkler et al.   |          |
| 6,494,844 | B1|   | 12/2002 | Van Bladel et al.|          |
| 6,558,382 | B2|   | 5/2003  | Jahns et al.     |          |
| 6,638,235 | B2|   | 10/2003 | Miller et al.    |          |
| 6,676,658 | B2|   | 1/2004  | Burbank et al.   |          |
| 6,712,775 | B2| * | 3/2004  | Burbank et al.   | 600/567  |
| 6,752,805 | B2|   | 6/2004  | Maguire et al.   |          |
| 6,758,824 | B1|   | 7/2004  | Miller et al.    |          |
| 6,790,636 | B1| * | 9/2004  | Star et al.      | 435/40.5 |
| 6,923,754 | B2|   | 8/2005  | Lubock           |          |

(Continued)

FOREIGN PATENT DOCUMENTS

EP    0161606    11/1985

(Continued)

OTHER PUBLICATIONS

PCT International Search Report #PCT/IB2006/053504 dated Apr. 2, 2007.

(Continued)

*Primary Examiner* — Sean Dougherty
(74) *Attorney, Agent, or Firm* — Vista IP Law Group LLP

(57) ABSTRACT

A system for treating a lesion site of a patient is disclosed. The system includes a cannula having a lumen, a conduit in communication with said lumen, an introducer stylet removably disposed within said cannula, a resecting device selectively insertable within said cannula, and an adjuvant treatment device selectively insertable within said cannula.

19 Claims, 36 Drawing Sheets

U.S. PATENT DOCUMENTS

| | | | |
|---|---|---|---|
| 6,945,942 | B2 | 9/2005 | Van Bladel et al. |
| 6,955,641 | B2 | 10/2005 | Lubock |
| 6,979,290 | B2 | 12/2005 | Mourlas et al. |
| 7,066,893 | B2 | 6/2006 | Hibner et al. |
| 7,150,712 | B2 * | 12/2006 | Buehlmann et al. ......... 600/114 |
| 7,179,232 | B2 | 2/2007 | Sutton et al. |
| 7,338,430 | B2 | 3/2008 | Lim et al. |
| 7,347,829 | B2 | 3/2008 | Mark et al. |
| 7,517,310 | B2 | 4/2009 | Lubock et al. |
| 7,618,362 | B2 | 11/2009 | DiCarlo et al. |
| 7,740,597 | B2 | 6/2010 | Cicenas et al. |
| 2002/0029007 | A1 | 3/2002 | Bryan et al. |
| 2002/0029060 | A1 | 3/2002 | Hogendijk |
| 2002/0161298 | A1 * | 10/2002 | Burbank et al. ............. 600/431 |
| 2002/0188196 | A1 * | 12/2002 | Burbank et al. ............. 600/431 |
| 2003/0083542 | A1 | 5/2003 | Alferness et al. |
| 2003/0093007 | A1 | 5/2003 | Wood |
| 2003/0097079 | A1 | 5/2003 | Garcia |
| 2003/0130575 | A1 * | 7/2003 | Desai ........................... 600/417 |
| 2003/0149327 | A1 | 8/2003 | Chin et al. |
| 2003/0212373 | A1 | 11/2003 | Hall et al. |
| 2004/0019299 | A1 | 1/2004 | Ritchart et al. |
| 2004/0024304 | A1 * | 2/2004 | Foerster et al. ............... 600/407 |
| 2004/0077938 | A1 | 4/2004 | Mark et al. |
| 2004/0077972 | A1 | 4/2004 | Tsonton et al. |
| 2004/0153003 | A1 | 8/2004 | Cicenas et al. |
| 2004/0236211 | A1 * | 11/2004 | Burbank et al. ............. 600/431 |
| 2004/0267154 | A1 | 12/2004 | Sutton et al. |
| 2005/0033195 | A1 * | 2/2005 | Fulton et al. .................. 600/562 |
| 2005/0059884 | A1 * | 3/2005 | Krag ............................. 600/424 |
| 2005/0165329 | A1 | 7/2005 | Taylor et al. |
| 2005/0182339 | A1 * | 8/2005 | Lee et al. ...................... 600/564 |
| 2005/0234336 | A1 * | 10/2005 | Beckman et al. ............. 600/431 |
| 2005/0240074 | A1 | 10/2005 | Lubock |
| 2005/0256508 | A1 | 11/2005 | Hall |
| 2006/0009712 | A1 | 1/2006 | Van Bladel et al. |
| 2006/0111605 | A1 | 5/2006 | Larsen et al. |
| 2006/0167416 | A1 | 7/2006 | Mathis et al. |
| 2006/0169293 | A1 * | 8/2006 | Yokoi et al. ................... 128/899 |
| 2006/0173296 | A1 | 8/2006 | Miller et al. |
| 2006/0217587 | A1 | 9/2006 | DiCarlo et al. |
| 2006/0260994 | A1 | 11/2006 | Mark et al. |
| 2007/0055282 | A1 | 3/2007 | Muschler |
| 2007/0142725 | A1 | 6/2007 | Hardin et al. |
| 2007/0203427 | A1 * | 8/2007 | Vetter et al. .................... 600/564 |
| 2007/0219460 | A1 | 9/2007 | Goldenberg |
| 2007/0293788 | A1 | 12/2007 | Entrekin et al. |
| 2008/0194985 | A1 * | 8/2008 | Nicoson et al. ............... 600/566 |
| 2008/0200834 | A1 | 8/2008 | Mark et al. |
| 2009/0217932 | A1 * | 9/2009 | Voegele ........................ 128/899 |

FOREIGN PATENT DOCUMENTS

| | | |
|---|---|---|
| GB | 1252170 | 11/1971 |
| WO | WO-01/82810 | 11/2001 |
| WO | WO2004/043531 | 5/2004 |

OTHER PUBLICATIONS

Reuters Heatlh publication entitled "Contrast mammography shows promise in cancer detection." author David Douglas.

Aunt Minnie.com publication entitled "TechniScan system completes phase I trials."

MSNBC Heath Publication entitled "Seeds may zap breast cancer." Author Robert Bazell.

Radiology Today—Technology Trends, article entitled "New Use for an Old Technology Applying Tomosynthesis to Mammography." Author Dan Harvey.

Biophontonics International—Imaging article entitled "Optoacoustics Moves Closer to the Clinic." Author Nadya Anscombe.

Office Action for U.S. Appl. No. 11/237,110 dated Jul. 8, 2008.

Amendment to Office Action for U.S. Appl. No. 11/237,110 dated Oct. 8, 2008.

Office Action Dated Jul. 9, 2008 for U.S. Appl. No. 12/061,344.

Amendment in Response to OA dated Jul. 9, 2008 for U.S. Appl. No. 12/061,344.

Final Office Action dated Jan. 28, 2009 for U.S. Appl. No. 12/061,344.

Response to Final Office for U.S. Appl. No. 12/061,344 dated Mar. 19, 2009.

Final Office Action dated Jan. 19, 2010 for U.S. Appl. No. 12/061,344.

Office Action dated Jun. 19, 2009 for U.S. Appl. No. 12/061,344.

Office Action dated May 7, 2009 for U.S. Appl. No. 11/237,110.

Amendment in Response to Office Action dated May 7, 2009 for U.S. Appl. No. 11/237,110.

Advisory Action dated Jul. 15, 2009 for U.S. Appl. No. 11/237,110.

Office Action dated Sep. 16, 2009 for U.S. Appl. No. 11/237,110.

Response to Office Action dated Jun. 19, 2009 for U.S. Appl. No. 12/061,344.

Response to Office Action dated Sep. 16, 2009 for U.S. Appl. No. 11/237,110.

Final Office Action dated Sep. 23, 2010 for U.S. Appl. No. 12/061,344.

Non-Final Office Action dated Oct. 25, 2010 for U.S. Appl. No. 12/061,195.

Non-Final Office Action dated Dec. 22, 2010 for U.S. Appl. No. 11/237,110.

Response to Final Office Action dated Sep. 23, 2010 for U.S. Appl. No. 12/061,344.

Response to Non-Final Office Action dated Oct. 25, 2010 for U.S. Appl. No. 12/061,195.

Final Office Action dated Mar. 2, 2010 for U.S. Appl. No. 11/237,110.

Response to Final Office Action Jan. 19, 2010 for U.S. Appl. No. 12/061,344.

Non-Final Office Action dated Apr. 12, 2010 for U.S. Appl. No. 12/061,344.

Response to Non-Final Office Action dated Apr. 12, 2010 for U.S. Appl. No. 12/061,344.

PCT International Search Report for PCT/IB07/54229 dated Jul. 9, 2010.

Response to Non-Final Office Action dated Mar. 2, 2010 for U.S. Appl. No. 11/237,110.

Final Office Action dated Mar. 22, 2011 for U.S. Appl. No. 12/061,195.

Response to Non-Final Office Action dated Dec. 22, 2010 for U.S. Appl. No. 11/237,110.

Response to Final Office Action dated Mar. 22, 2011 for U.S. Appl. No. 12/061,195.

Non-Final Office Action dated Aug. 26, 2011 for U.S. Appl. No. 12/061,195.

* cited by examiner

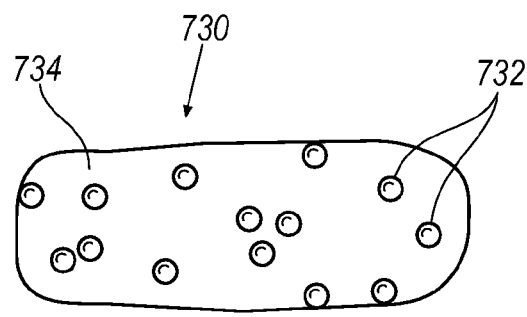 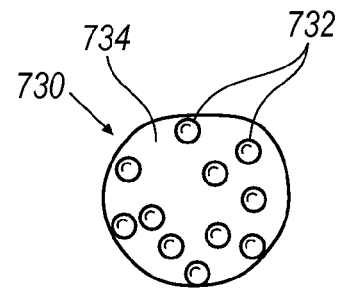
FIG. 43A    FIG. 43B
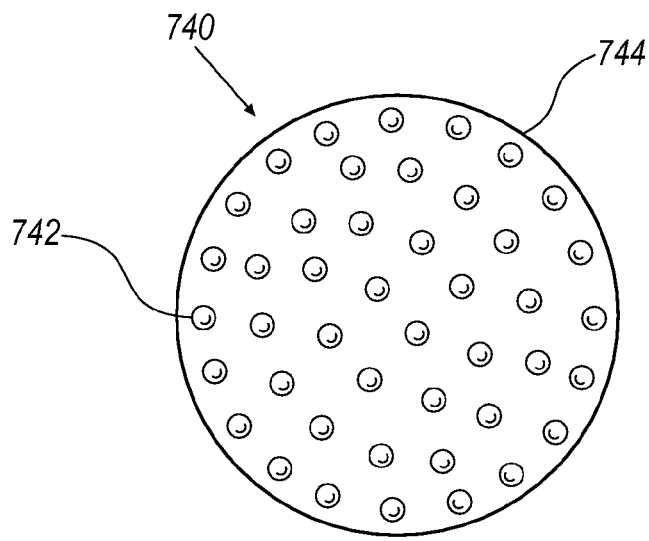
FIG. 43C
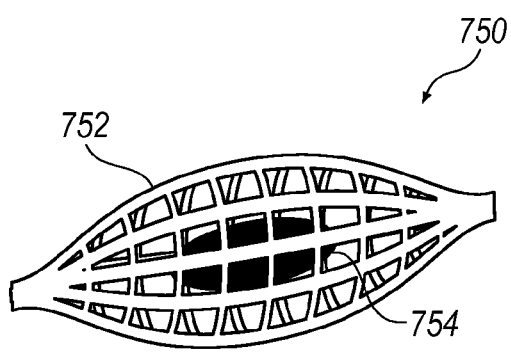 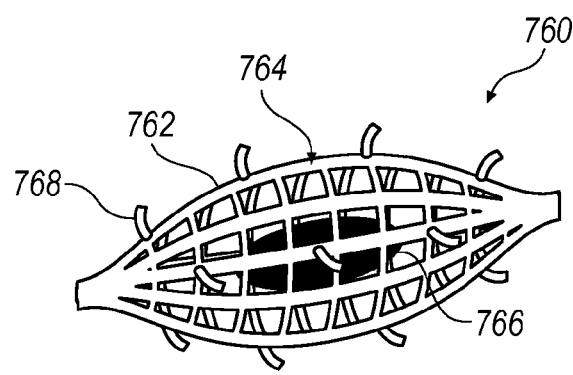
FIG. 44    FIG. 45

SYSTEM AND METHOD FOR MINIMALLY INVASIVE DISEASE THERAPY

RELATED APPLICATIONS

The present application is a continuation in part application of U.S. patent application Ser. No. 11/237,110 filed on Sep. 28, 2005, entitled "System and Method for Minimally Invasive Disease Therapy," the contents of which are incorporated herein by reference in its entirety.

FIELD OF THE INVENTION

The present invention relates generally to a surgical system and method for removing and treating diseased tissue and more particularly to a minimally invasive system and method for removing diseased tissue and creating a margin around an excised area.

BACKGROUND

Description of the Related Art

Surgical cancer treatments have advanced to two primary stages. A first stage removes the cancerous tissue by resecting the tissue from the body. The goal of the first stage is to remove all cancerous cells from a target area. However, unless a large portion of healthy tissue is also resected, a possibility exists that some cancerous cells remain near the resection site.

A second stage typically involves a broad-based radiation therapy to the cancerous region. The radiation therapy is necessary to destroy any cancerous tissue that may have remained in the targeted area after resection. However, broad-based radiation therapy requires multiple exposures to high doses of radiation. Such exposure results in undesirable side effects and the exposure may not be limited to the tissues that surrounded the resected tissue. Further, a full course of treatment may require six weeks of individual treatments that result in frequent visits to a hospital or treatment suite.

Accordingly, an improved treatment method is desired that improves treatment effectiveness, reduces side effects, reduces treatment time, avoids widespread exposure to radiation, and is verifiable using medical imaging techniques. Additionally, an improved treatment method is desired that may be used with multiple imaging modalities, these modalities may include Magnetic Resonance Imaging (MRI), ultrasound, and x-ray Computed Tomography (CT).

SUMMARY

A system for treating a lesion site of a patient is disclosed. In one embodiment the system includes a cannula having a lumen, a conduit in communication with the lumen, an introducer stylet removably disposed within the cannula, a resecting device selectively insertable within the cannula, and an adjuvant treatment device selectively insertable within the cannula. In an alternative embodiment, a tissue cavity is subject to brachytherapy.

A method of treating a lesion site of a patient is also disclosed. The method includes the steps of inserting an introducer stylet having an outer cannula disposed thereon into a patient's body creating a pathway to a lesion site, removing the introducer stylet from the patient's body leaving behind the outer cannula. The method may further include inserting a resection device into the patient's body through the outer cannula and removing tissue from the lesion site, removing the resection device from the patient's body leaving behind the outer cannula. Further, the method may include inserting an adjuvant therapy device into the patient's body through the outer cannula, and treating the lesion site using the adjuvant therapy device.

BRIEF DESCRIPTION OF THE DRAWINGS

The features and inventive aspects of the present invention will become more apparent upon reading the following detailed description, claims, and drawings, of which the following is a brief description:

FIG. 43A shows a side cross-section of treatment pellets dispersed in a material;

FIG. 43B shows a front cross section of treatment pellets dispersed in a material;

FIG. 43C shows front cross section of treatment pellets dispersed in a material in an alternative embodiment, the pellets being evenly spaced apart;

FIG. 44 shows a caged treatment seed;

FIG. 45 shows a caged treatment seed wherein the cage includes barbs such that the cage and seed do not migrate once deployed;

DETAILED DESCRIPTION

Figure 1:
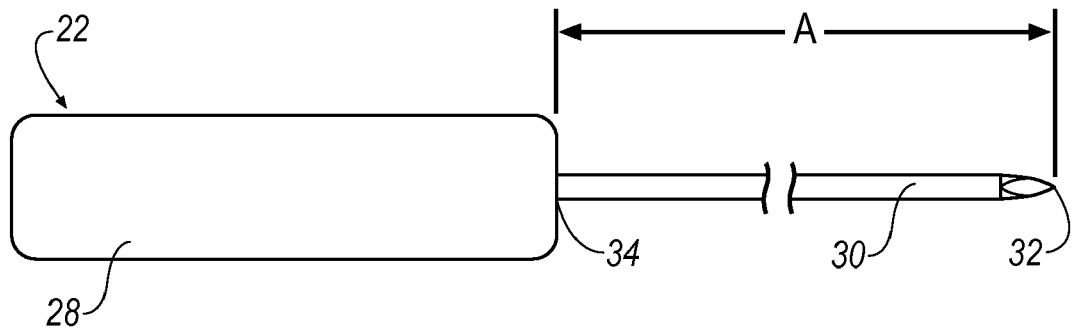
FIG. 1 is a side view of an introducer stylet in accordance with an embodiment of the present invention.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Figure 2:
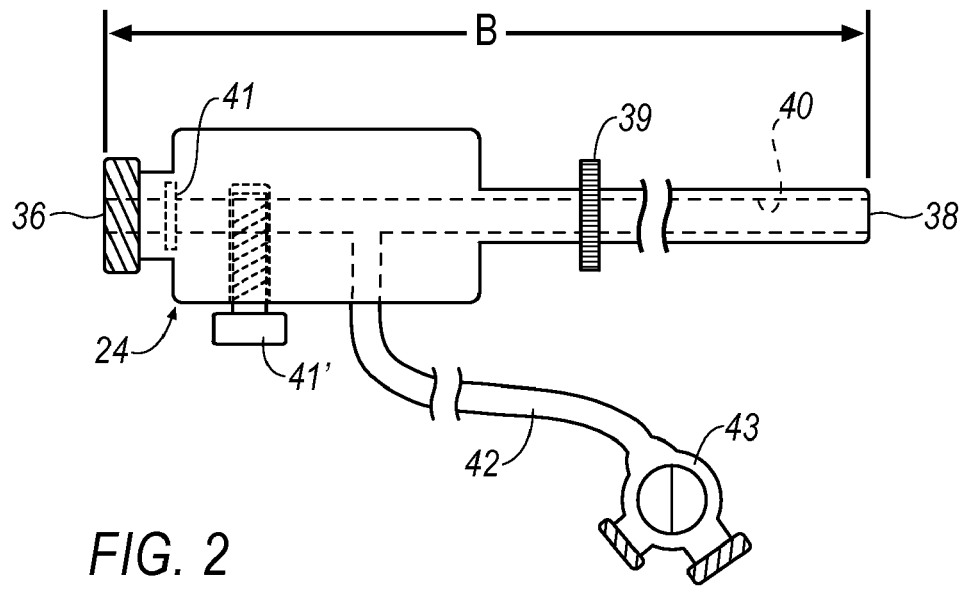
FIG. 2 is a side view of an outer cannula and fluid conduit in accordance with the embodiment of FIG. 1.
Figure 3:
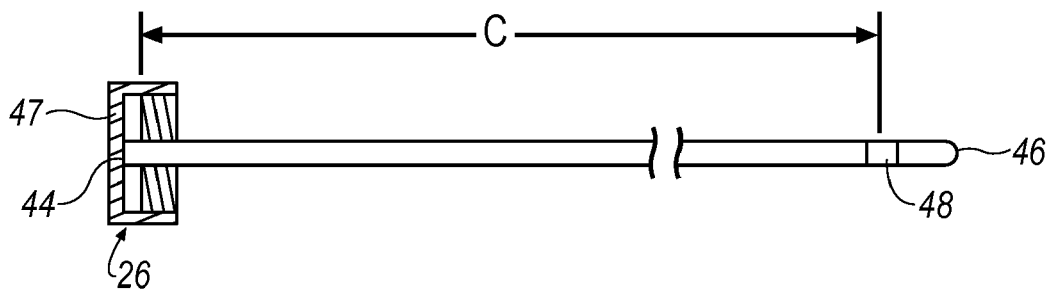
FIG. 3 is a side view of a target confirmation device in accordance with the embodiment of FIG. 1.

Referring to FIGS. 1-3, a medical system 20 is shown that includes an introducer stylet 22, an outer cannula 24 and a target confirmation device 26. As will be described in detail, system 20 is particularly, but not necessarily, suited for use in biopsy procedures that identify the target biopsy site using Magnetic Resonance Imaging (MRI) or a comparable medical imaging modality. A system similar to system 20 can be seen by way of example in pending U.S. patent application Ser. No. 10/649,068, which is owned by the assignee of the present invention and is incorporated herein by reference in its entirety.

In one embodiment, introducer stylet 22 includes a handle 28 and a stylet 30 having a distal end 32 and a proximal end 34 connected to handle 28. Handle 28 may be made of a medical grade resin or other MRI compatible material. Stylet 30 may also be made of an MRI compatible, medical grade material, such as 316 stainless steel or inconel 625.

In one particular configuration, distal end 32 of stylet 30 may be provided with a tissue piercing tip, such as a trocar tip, to facilitate penetration of stylet 30 into a patient's tissue. In addition to a trocar tip, it will be appreciated that stylet 30 may include other devices for piercing the patient's tissue, including without limitation, devices that use a laser, radiofrequencies (RF), or ultrasonics to pierce the tissue. The length of stylet 30 is generally denoted by the reference character "A" in FIG. 1.

Referring to FIG. 2, an embodiment of outer cannula 24 is shown. Outer cannula 24 extends from an open proximal end 36 to an open distal end 38, which is separated from proximal end 36 by a distance generally denoted by the reference character "B". Like introducer stylet 30, outer cannula 24 may be made from a medical grade resin or other MRI compatible material. In some configurations, proximal end 36 may include a luer-style fitting or other suitable configuration for interfacing, but not necessarily connecting, outer cannula 24 with target confirmation device 26. A depth limiting member 39, such as, for example, a rubber o-ring, may be moveably disposed on outer cannula 24 to limit the insertion depth of outer cannula 24 into the patient's body.

In one embodiment, outer cannula 24 may also include an inner lumen 40 therethrough, which is open to communication with a fluid conduit 42 for supplying fluids, such as saline and anesthetics, or removing fluids, such as blood, from the patient's body. Fluid conduit 42 communicates with inner lumen 40 via a port in outer cannula 24. In some configurations, outer cannula 24 may include a haemostatic valve, depicted generally as element 41, or a manually operable valve 41' that can be selectively closed to prevent the escape of fluid from proximal end 36. Fluid conduit 42 may also include a directional valve 43 to selectively control the supply and removal of fluid to and from inner lumen 40, respectively.

In FIG. 3, an embodiment of target confirmation device 26 is depicted. Target confirmation device 26 is an elongated member that is sized to fit within inner lumen 40 of outer cannula 24. Target confirmation device 26, which may be made of a medical grade resin or other MRI compatible material, extends from a connecting end 44 to a distal end 46. Connecting end 44 may be configured with a cap 47 that abuts proximal end 36 of outer cannula 24 when target confirmation device 26 is inserted into outer cannula 24. In some configurations, cap 47 may include a luer-style fitting or other suitable feature for interfacing, but not necessarily connecting, target confirmation device 26 with outer cannula 24.

Distal end 46 of target confirmation device 26 may be generally rounded to facilitate entry into the patient's body. In one embodiment, a portion of target confirmation device 26 is configured with a magnetic resonance imaging (MRI) identifiable material, such as inconel 625, titanium or other material with similar magnetic characteristics. In one particular configuration, a targeting band 48 is provided a distance "C" from connecting end 44, as shown in FIG. 3; the distance "C" being measured from the approximate center of targeting band 48 to connecting end 44 (or the inside of cap 47), for example. Targeting band 48 provides a reference point in an MR image relative to the target biopsy tissue.

In another embodiment of target confirmation device 26, the tip of target confirmation device 26 itself may be used to provide the reference point in the MR image, provided the target confirmation device material exhibits a relatively low artifact during MR imaging. As used herein, the term "artifact" describes a material's tendency to distort an MR image. A material exhibiting a relatively high artifact will render the body tissue surrounding the material unreadable in an MR image. Conversely, a material with a relatively low artifact or signal void will allow the material to be readily identified in the MR image and will not significantly distort the MR image of the surrounding tissue.

Figure 3A:
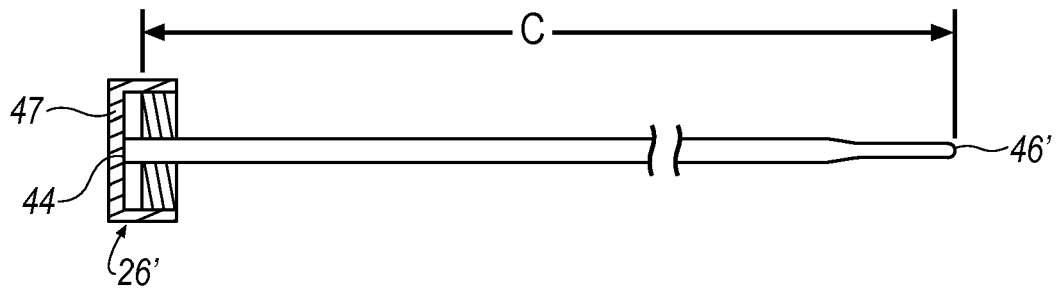
FIGS. 3A and 3B are side views of target confirmation devices according to alternate embodiments of the present invention.
Figure 3B:
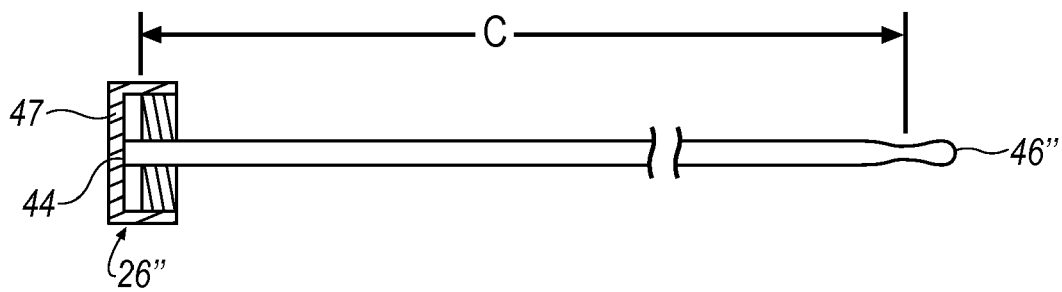

As shown in the embodiments of FIGS. 3A and 3B, distal end 46', 46" of target confirmation device 26', 26" may include a particular shape to help identify the location of target confirmation device 26 relative to the surrounding tissue. In the embodiment of FIG. 3A, a portion of target confirmation device 26' adjacent distal end 46' has a smaller diameter relative to the remaining length. Alternatively, in the embodiment of FIG. 3B, a portion of target confirmation device 26" has a tapered distal end 46" to provide an hour glass like image when viewed under MR. It will be appreciated that the target confirmation devices represented in FIGS. 3, 3A and 3B are not limited to the configurations shown, and that other configurations are with in the scope of the present invention.

In still another embodiment, stylet 30 may function as a target confirmation device. In this embodiment, introducer stylet 22, and more particularly stylet 30, may be made of an MRI compatible material that preferably, but not necessarily, exhibits a relatively low artifact.

Figure 4:
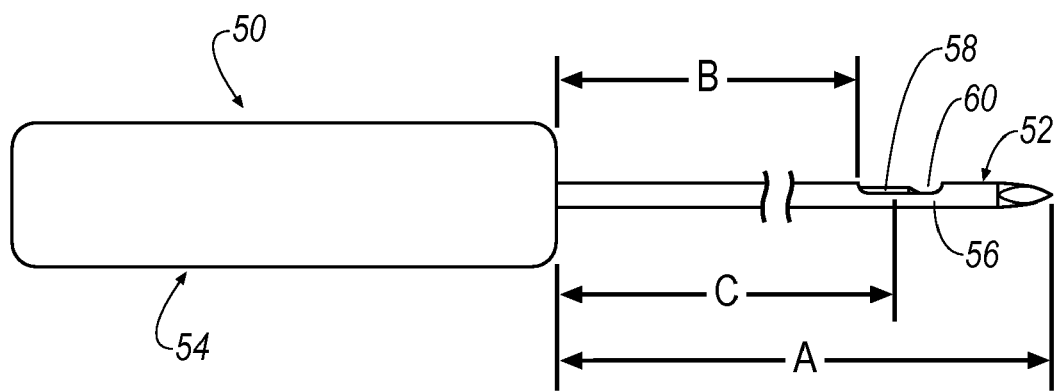
FIG. 4 is a side view of an exemplary biopsy device for use with an introduction system of the present invention.
Figure 5:
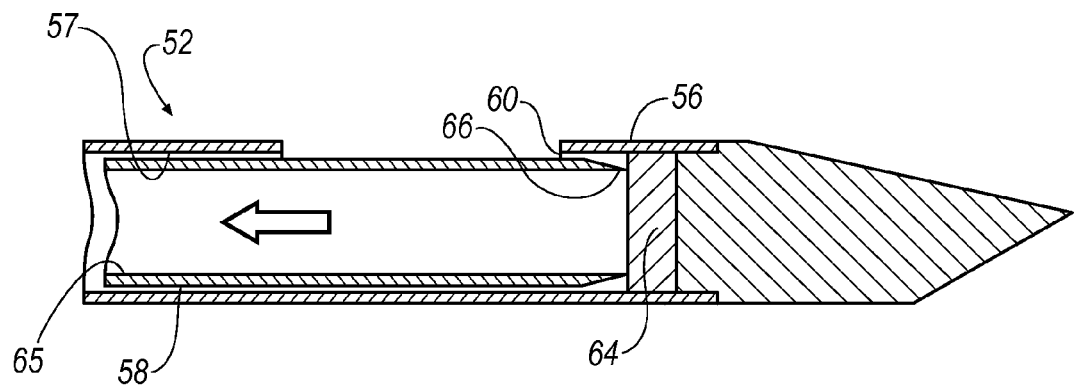
FIG. 5 is a detailed cross sectional view of a cutting element of the biopsy device of FIG. 4.

An exemplary resection apparatus 50, which is suitable for use with system 20 of the present invention, is generally shown in FIG. 4 and in more detail in FIG. 5. Resection apparatus 50 includes a cutting element 52 sized for introduction into a handpiece 54. The exemplary resection apparatus 50 is configured as a "tube-within-a-tube" cutting device. More particularly, cutting element 52 includes an outer cannula 56 having an outer lumen 57 and an inner cannula 58 sized to fit concentrically within the outer lumen. A motor or other motion generating device is provided within handpiece 54 to rotate and/or translate inner cannula 58 within outer cannula 56. A biopsy apparatus similar to resection apparatus 50 can be seen by way of example in pending U.S. patent application Ser. Nos. 09/707,022 and 09/864,031, which are owned by the assignee of the present invention and are incorporated herein by reference in their entirety.

One embodiment of a working end of cutting element 52 is depicted in FIG. 5. In the illustrated embodiment, outer cannula 56 defines a tissue-receiving opening 60, which communicates with outer lumen 57. The working end of cutting element 52 may further include a cutting board 64 that is disposed within outer lumen 57 at the distal end of outer cannula 56. Inner cannula 58 defines an inner lumen 65 that is hollow along its entire length to provide for aspiration of the biopsy sample (tissue). Inner cannula 58 terminates in a cutting edge 66 that may be formed by an inwardly beveled surface having a razor-sharp edge.

Figure 6:
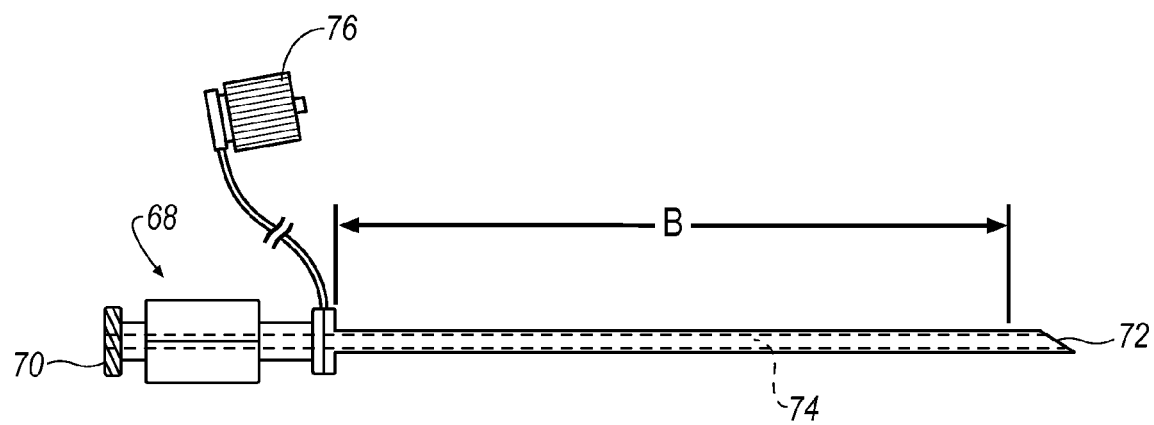
FIG. 6 is a side view of an aspiration wand suitable for insertion into the outer cannula of FIG. 2.

Referring to FIG. 6, a wand 68 is shown that can be inserted into outer cannula 24 after resection apparatus 50 has been removed, or at any time outer cannula 24 is free of obstruction. In one embodiment, wand 68 extends from a connecting end 70 to an insertion end 72 and includes a lumen 74 that extends from connecting end 70 to insertion end 72. Connecting end 70 may include a luer interface or other suitable fitting for connecting wand 68 to a vacuum source (not shown) or a fluid source (not shown). Wand 68 may also include a cap 76 that can be placed onto connecting end 70 to inhibit fluid leakage when wand 68 is inserted into the patient. The haemostatic valve 41 in outer cannula 24 seals against wand 68, as it does against target confirmation device 26 and resection apparatus 50, when inserted into outer cannula 24. Additionally, the outside diameter of wand 68 is preferably less than the inside diameter of inner lumen 40 to allow the passage of fluids through fluid conduit 42 to pass into or out of the patient's body. When cap 76 is removed and wand 68 is connected to a vacuum source, fluids, such as blood and saline, can be aspirated from the biopsy site or, conversely, when connected to a fluid source, fluids can be delivered to the biopsy site.

Figure 7:
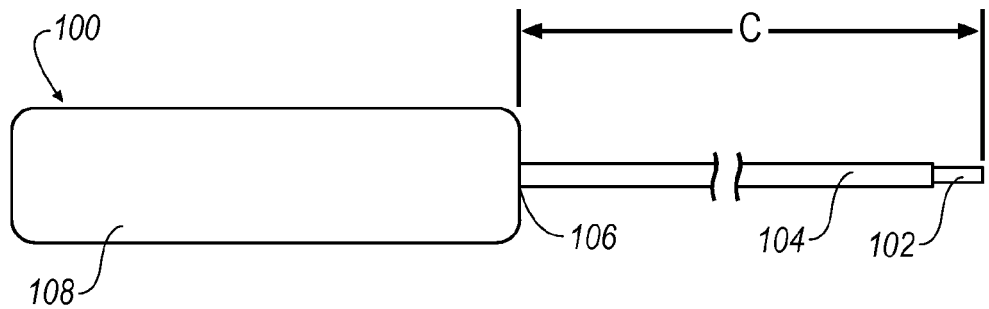
FIG. 7 is a side view of a treatment device wand suitable for insertion into the outer cannula of FIG. 2.

Referring to FIG. 7, a treatment device 100 is shown that can be inserted into outer cannula 24. In one embodiment, treatment device 100 includes a treatment tip 102 sized for introduction into the patient's body, a treatment shaft 104 having a proximal end 106, and a treatment handpiece 108. A fluid system, electrical system, or other supporting elements may be attached to, or operate in cooperation with, treatment handpiece 108 in order to effectuate an adjuvant treatment at treatment tip 102 (to be explained in further detail with respect to FIGS. 8-11).

Figure 8:
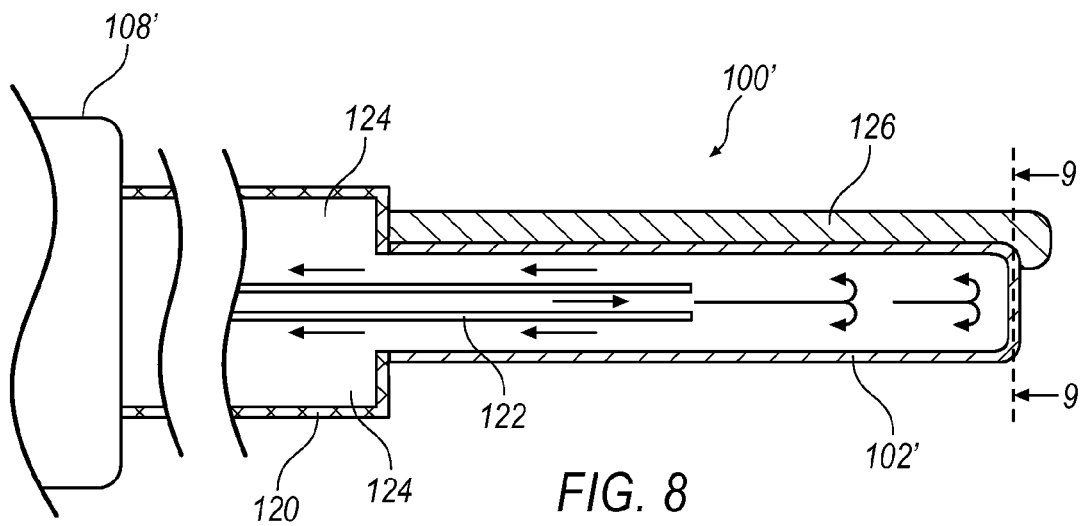
FIG. 8 is a cross-sectional view of a cryo-ablation treatment device for use with the treatment device wand of FIG. 7.
Figure 9:
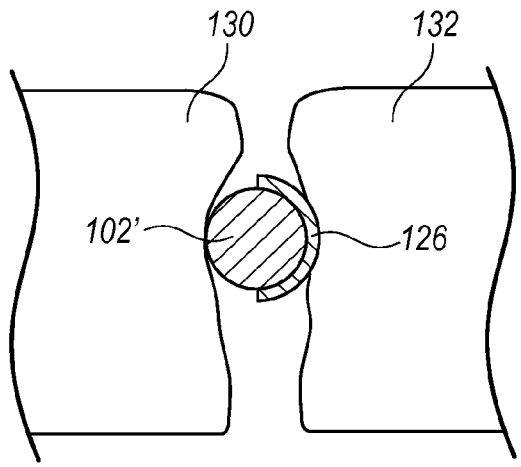
FIG. 9 is a cross-sectional view of the cryo-ablation treatment device of FIG. 8 as used in a medical procedure.

An alternative embodiment of treatment device 100' is depicted in FIG. 8. Treatment device 100' is a cryo-ablation device. Treatment device 100', utilizing cryo-ablation, is a surgical technique using extremely cold temperatures to destroy cells. In the illustrated embodiment, treatment device 100' includes an inner cannula 120 sized to fit within outer cannula 24 of system 20. Treatment tip 102' is sized to extend beyond distal end 38 of outer cannula 24 and directly interface the patient's tissue. A supply tube 122 extends from treatment handpiece 108' through inner cannula 120 and provides freezing liquid to treatment tip 102'. The freezing liquid exits treatment tip 102' through a return cavity 124 defined as a region between inner cannula 120 and supply tube 122. Treatment tip 102' is configured to directly interface the patient's tissue and deliver the freezing treatment to the tissue surrounding treatment tip 102'.

Additionally, treatment tip 102' may include a shield 126 that allows for a portion of the tissue surrounding treatment tip 102' to be substantially protected from the freezing treatment. Thus, a surgeon may use shield 126 in sensitive areas so that undesired damage does not occur to sensitive tissues. For example, as illustrated in more detail in FIG. 9, treatment tip 102' is used between a target tissue 130 and a protected tissue 132. In this example, a surgeon may intend target tissue 130 to receive the cryo-ablation from treatment tip 102'. However, a sensitive tissue, such as an intestinal wall or skin, may not be able to withstand the treatment. In the case of an intestinal wall, the freezing may create an opening that may cause leakage and infection. Similarly, the skin may become damaged and a breaking of the skin may result. In these cases, shield 126 insulates protected tissue 132 from the freezing effects.

Figure 10:
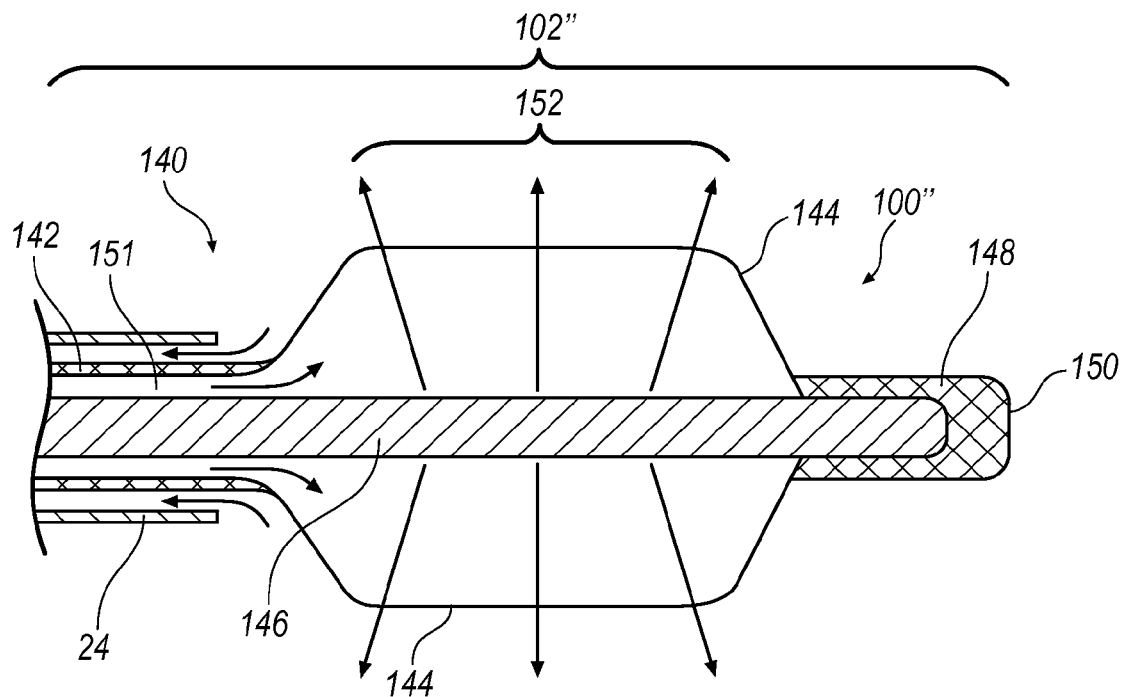
FIG. 10 is a cross sectional view of a photodynamic treatment device for use with the treatment device wand of FIG. 7.

Another alternative embodiment of treatment device 100" having treatment tip 102" is embodied as a photodynamic treatment device 140 as illustrated in FIG. 10. Photodynamic treatment device 140 includes a support shaft 142 sized to fit within outer cannula 24 of system 20, a balloon 144 configured for inflation when extended beyond outer cannula 24 of system 20, an optic guide 146 configured to deliver light, and a cap 148 configured to secure balloon 144 and optic guide 146 at a distal end 150. Photodynamic treatment device 140 utilizes a light source and, if desired, a photosensitizing agent to effectuate destruction of tissue at a desired location.

In operation, balloon 144 is inflated by a high pressure provided by an inflation channel 151 positioned between optic guide 146 and support shaft 142. Once inflated, balloon 144 is pressed against the surrounding tissue and a high power light source is activated. Photodynamic treatment device 140 then provides emitted light 152 to the treatment location. The heating effects of emitted light 152 may alone be sufficient for treatment. However, if desired, a photosensitizing agent may be applied to the treatment location to improve the destructive effect of emitted light 152. The photosensitizing agent may be applied before the surgical procedure, or alternatively, be applied locally by wand 68. When a photosensitizing agent is used, emitted light 152 interacts with the agent providing enhanced tissue destruction. Further, the photosensitizing agent may be configured to have an affinity for cancerous cells. Thus, damage to healthy tissues is further reduced.

Figure 11:
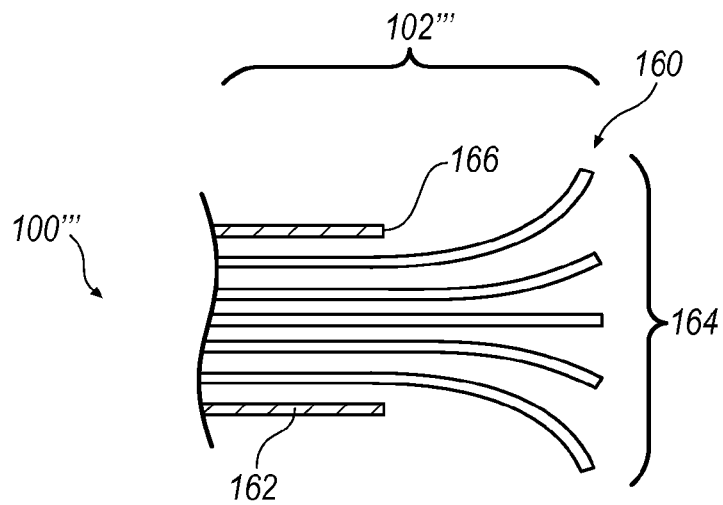
FIG. 11 is a side view of a radiofrequency treatment device for use with the treatment device wand of FIG. 7.

Another alternative embodiment of treatment device 100''' having treatment tip 102' is a radiofrequency ablation device 160 as illustrated in FIG. 11. Radiofrequency ablation device 160 includes a delivery cannula 162 sized to fit within outer cannula 24 of system 20 and one or more probes 164 configured to deliver radiofrequency energy to surrounding tissue. When inserting delivery cannula 162 in outer cannula 24 of system 20, probes 164 are retracted within delivery cannula 162. After reaching the appropriate depth to access the treatment location, probes 164 are extended beyond a distal end 166 of delivery cannula 162. After extension, probes 164 are in communication with the surrounding tissue and may be energized to effectuate treatment.

Yet another alternative embodiment of treatment device 100 includes a laser ablation device that utilizes heat to ablate tissue.

Still another alternative embodiment of treatment device 100 includes the use of localized interstial brachytherapy. In using this approach, a radioactive substance is provided interstially via balloon systems, one or more radioactive seeds, or the like, which may be placed (either temporarily or permanently) at the suspect tissue.

Referring to FIGS. 12-21, a medical procedure of the present invention will be described. In one embodiment, system 20 is employed to provide adjuvant treatment of a target tissue 80 within a patient's body 170. Target tissue 80, or lesion, to be biopsied and/or removed and subsequently adjuvantly treated is located using a medical imaging system, such as MRI or other suitable imaging modalities. A reference structure 172 may be positioned adjacent patient's body 170 to assist in locating the target tissue 80. The location of target tissue 80 relative to reference structure 172 may be determined along one or more axes. In the illustrated embodiment, the location of target tissue 80 relative to reference structure 172 is determined along the X and Y axes; however, the target tissue 80 location may also be determined along all three of the X, Y, and Z axes. While the described method employs reference structure 172 to locate target tissue 80, reference structure 172 is not necessarily required and a more "free-hand" approach may be utilized.

In an embodiment, reference structure 172 includes a support grid having a number of holes therethrough. Each hole is sized to allow passage of outer cannula 24. The hole through which outer cannula 24 is ultimately inserted is determined by the location of target tissue 80 relative to reference structure 172 along the X and Y axes. Patient's body 170 and reference structure 172 are viewed using a medical imaging system, such as MRI, to determine the location of target tissue 80 relative to reference structure 172.

Figure 12:
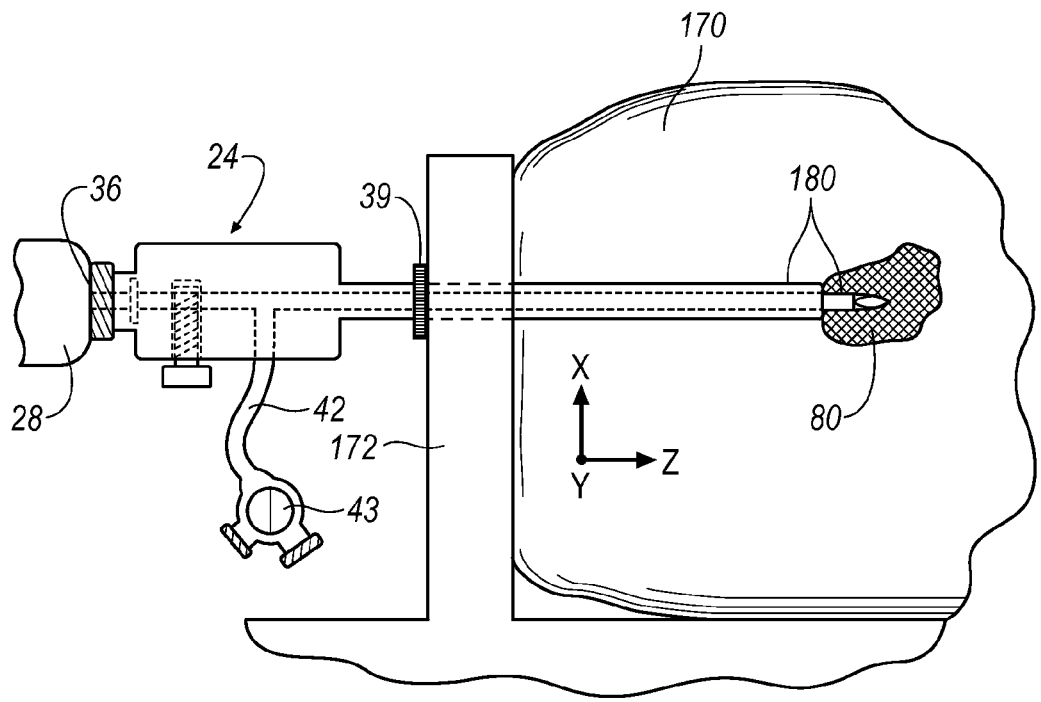
FIGS. 12-21 are elevational views illustrating different stages of a medical procedure using the medical system of the present invention.

After application of anesthesia, the stylet portion of introducer stylet 22 and a portion of outer cannula 24 are inserted through the support grid and into patient's body 170, creating a pathway 180 to target tissue 80 (see, e.g., FIG. 12). Introducer stylet 22 is then removed from patient's body 170 leaving behind outer cannula 24 and pathway 180 (see, e.g., FIG. 13).

Fluids may be inserted into or removed from patient's body 170 through inner lumen 40 via fluid conduit 42. These fluids may include, for example, additional anesthetics and/or saline solution to cleanse pathway 180 and remove blood. Accumulated blood and other fluids within pathway 180 may be aspirated through fluid conduit 42 or by inserting wand 68 prior to insertion of target confirmation device 26, 26', 26".

Figure 13:
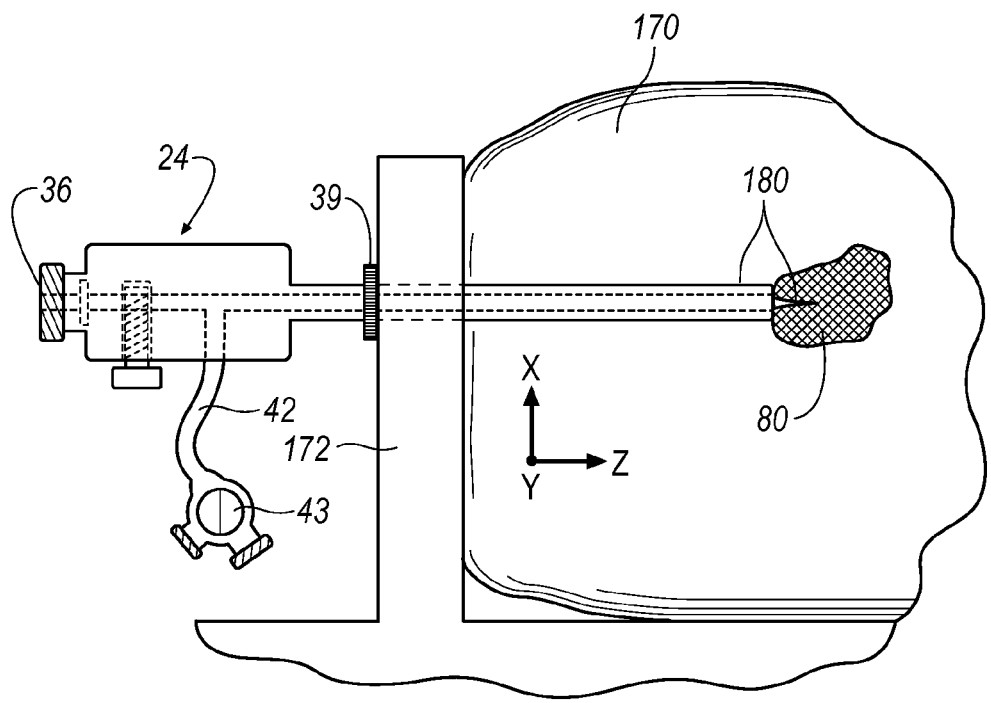
Figure 14:
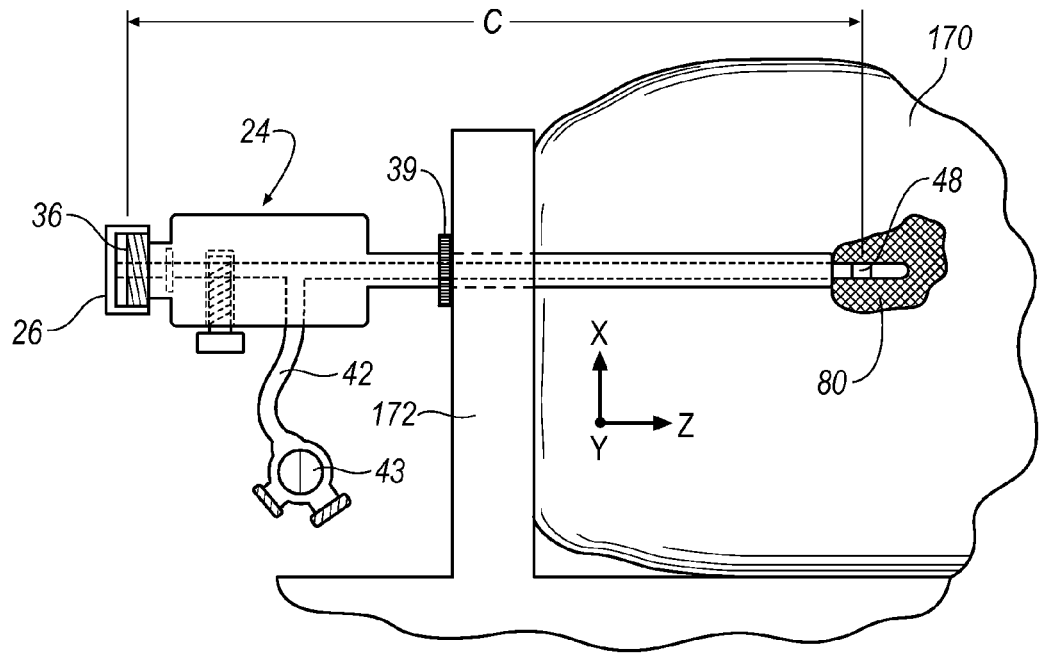

Once introducer stylet 22 is removed from outer cannula 24, target confirmation device 26, 26', 26" may be inserted into patient's body 170 through the path 180 created by outer cannula 24 (see, e.g., FIGS. 13 and 14). With target confirmation device 26, 26', 26" properly inserted into outer cannula 24, an image of the target site is again taken to determine the location of targeting band 48 or distal end 46', 46" in relation to target tissue 80 and reference structure 172. If targeting band 48 or distal end 46', 46" is in the desired position adjacent target tissue 80 along the Z-axis, target confirmation device 26, 26', 26" is removed from outer cannula 24. However, if targeting band 48 or distal end 46', 46" is not in the desired position, then the position of target confirmation device 26, 26', 26" and outer cannula 24 is modified along the Z-axis until the desired position is achieved.

Once the desired position is achieved, depth limiting member 39 is moved against reference structure 172 to inhibit movement of outer cannula 24 further into patient's body 170. When no reference structure 172 is used, depth limiting member may be moved directly against the patient's skin. Target confirmation device 26, 26', 26" is then removed from outer cannula 24 and resection apparatus 50 is inserted into outer cannula 24 until handpiece 54 abuts proximal end 36 of outer cannula 24.

Figure 15:
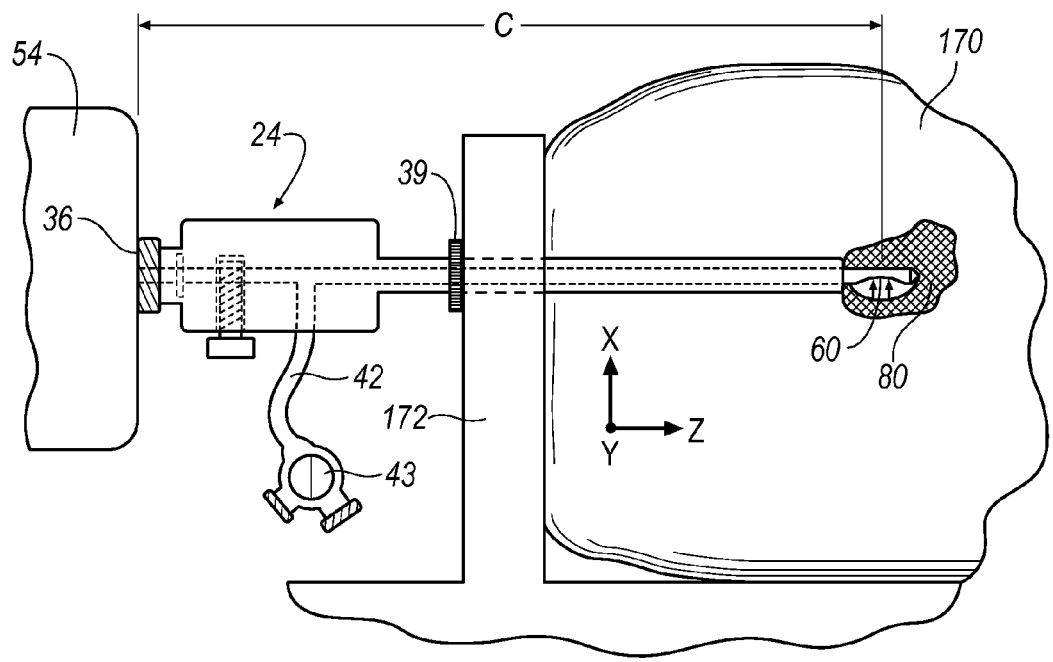

In the embodiment illustrated in FIG. 15, one or more samples of target tissue 80 are removed from patient's body 170 through tissue-receiving opening 60. The correct position of tissue-receiving opening 60 is ensured because the distance "C" between connecting end 44 of target confirmation device 26, 26', 26" and targeting band 48 (see, e.g., FIGS. 3 and 14), or the distance between connecting end 44 and the predetermined location on target confirmation device 26, 26', 26" (FIGS. 3, 3A, 3B), is approximately equal to the distance between the center of tissue-receiving opening 60 and handpiece 54 of resection apparatus 50.

Figure 16:
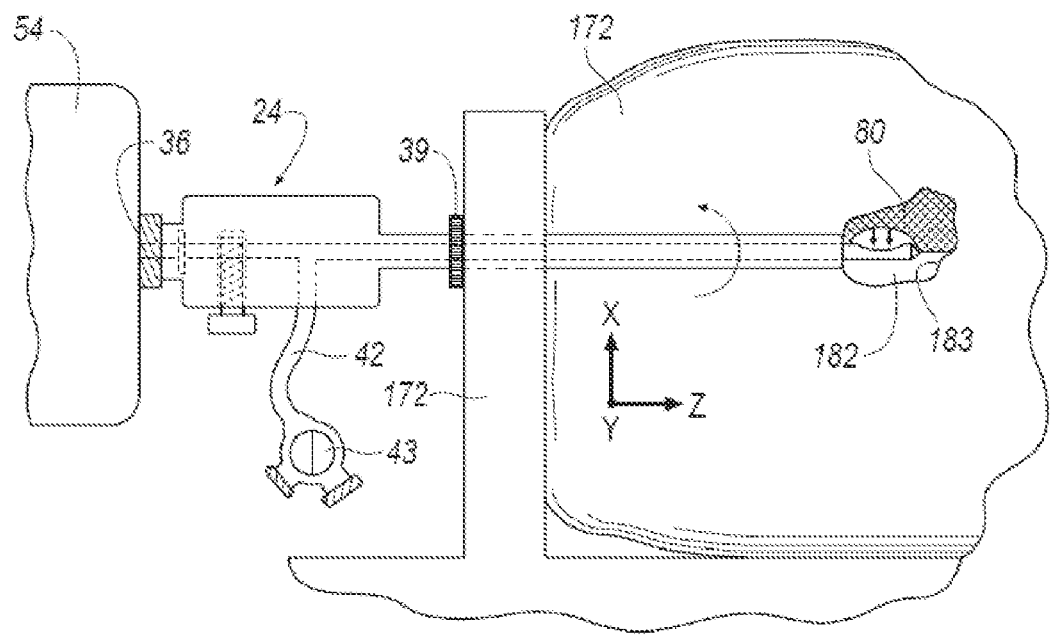

FIG. 16 illustrates the use of resection apparatus 50 for debulking a region of tissue where target tissue 80 is a significant region. In this case, resection apparatus 50 may be rotated and used to debulk the entire region of target tissue 80. As illustrated, resection apparatus 50 has been rotated leaving a void 182 having an inner wall 183, and is used to resect the remaining portion of target tissue 80.

Generally, the debulking procedure may be used where suspicion of cancerous tissue exists, or where treatment of a previously resected region is desired. In the case where a biopsy has previously been taken, the debulking process removes any hematomas that may have developed due to the biopsy or earlier procedure. In addition to resection of suspect tissues, removal of fluids and hematomas improves the efficacy of the adjuvant treatment because any fluids or hematomas act as insulators to adjuvant treatment such as cryoablation and reduce the effectiveness of the freezing penetration.

Figure 17:
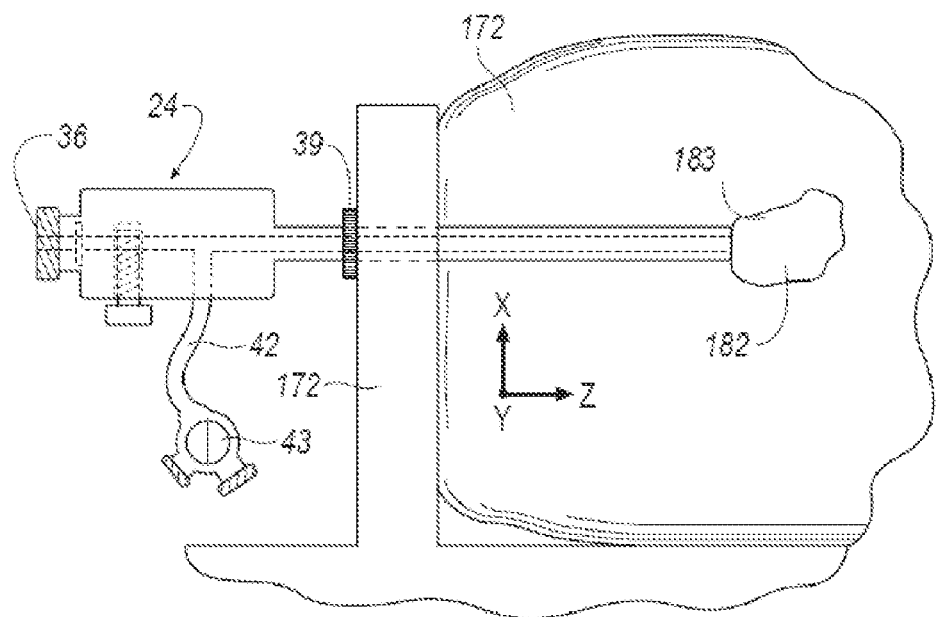

When resection of target tissue 80 is complete, resection apparatus 50 is removed from patient's body 170 leaving void 182 (see, e.g., FIG. 17). Treatment device 100, 100', 100", 100'" may then be inserted into patient's body 170 through outer cannula 24 (see, e.g., FIGS. 7 and 18). Treatment tip 102, 102', 102", 102'" is correctly positioned within void 182 because the distance "C" between connecting end 44 of target confirmation device 26, 26', 26" and targeting band 48 or distal end 46', 46" (see, e.g., FIGS. 3 and 14) is approximately equal to the distance between the center of tissue-receiving opening 60 and handpiece 54 of resection apparatus 50, and is approximately equal to the distance between a predetermined portion of treatment tip 102, 102', 102", 102'" and treatment handpiece 108 of treatment device 100, 100', 100", 100'" (FIG. 7).

Figure 18:
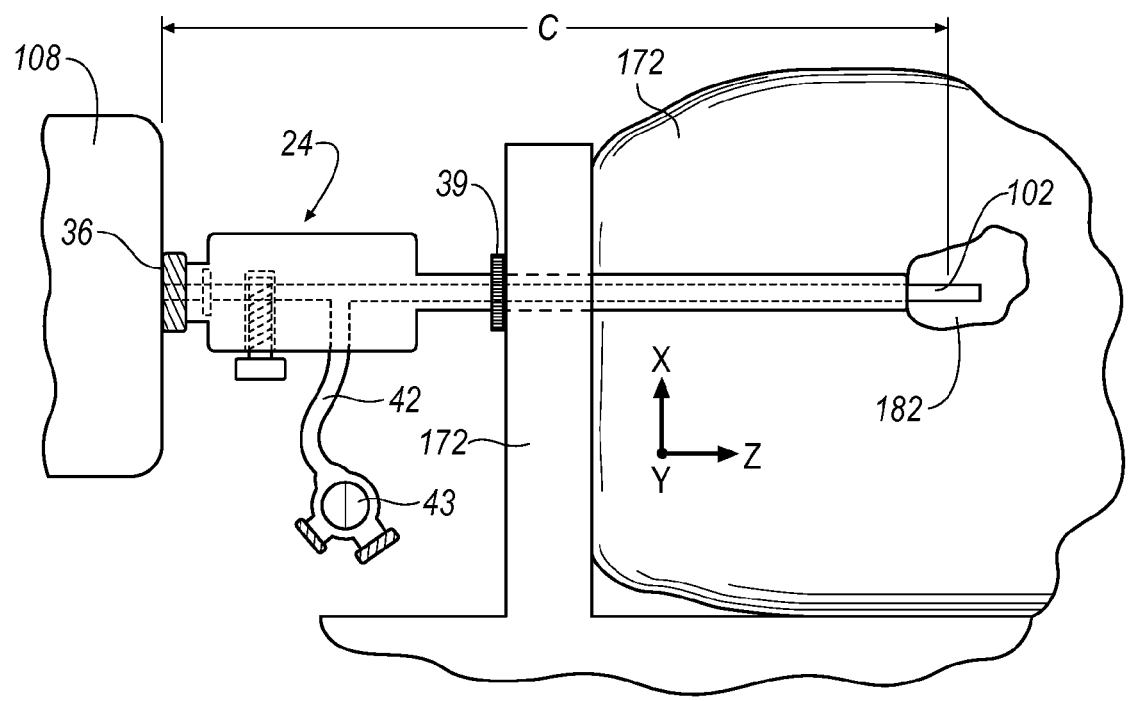
Figure 19A:
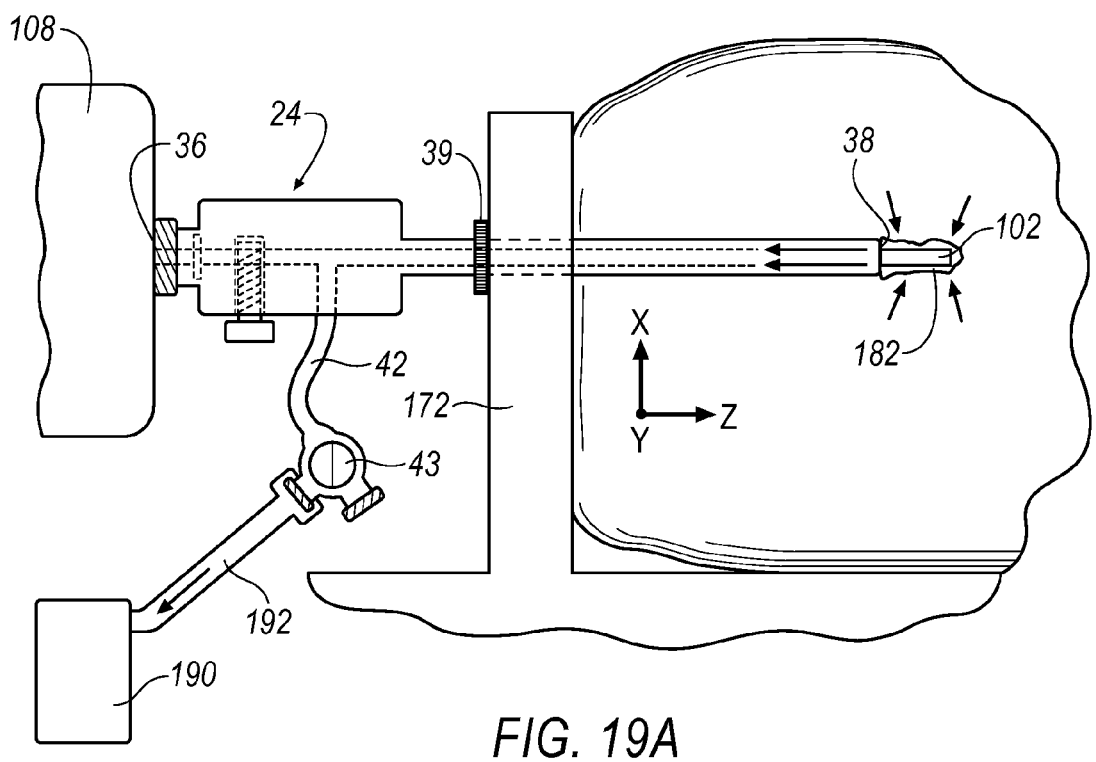
Figure 19B:
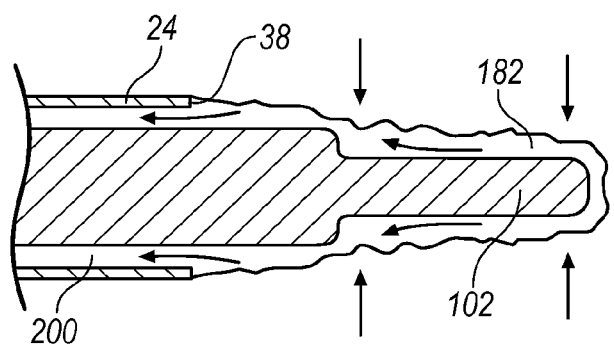

With treatment device 100, 100', 100", 100'" inserted into patient's body 170 (see FIG. 18), a vacuum device 190 may be attached to fluid conduit 42 by a vacuum hose 192 (see FIG. 19A). A surgeon may then operate vacuum device 190 to create a vacuum though lumen 40 of outer cannula 24. The vacuum through lumen 40 draws tissue close to open distal end 38 and collapses void 182 around treatment tip 102, 102', 102", 102'". FIG. 19B illustrates the collapsing of void 182 around treatment tip 102, 102', 102", 102'". A gap 200 between treatment tip 102, 102', 102", 102'" and outer cannula 24 provides a path for the vacuum to collapse void 182.

Figure 20A:
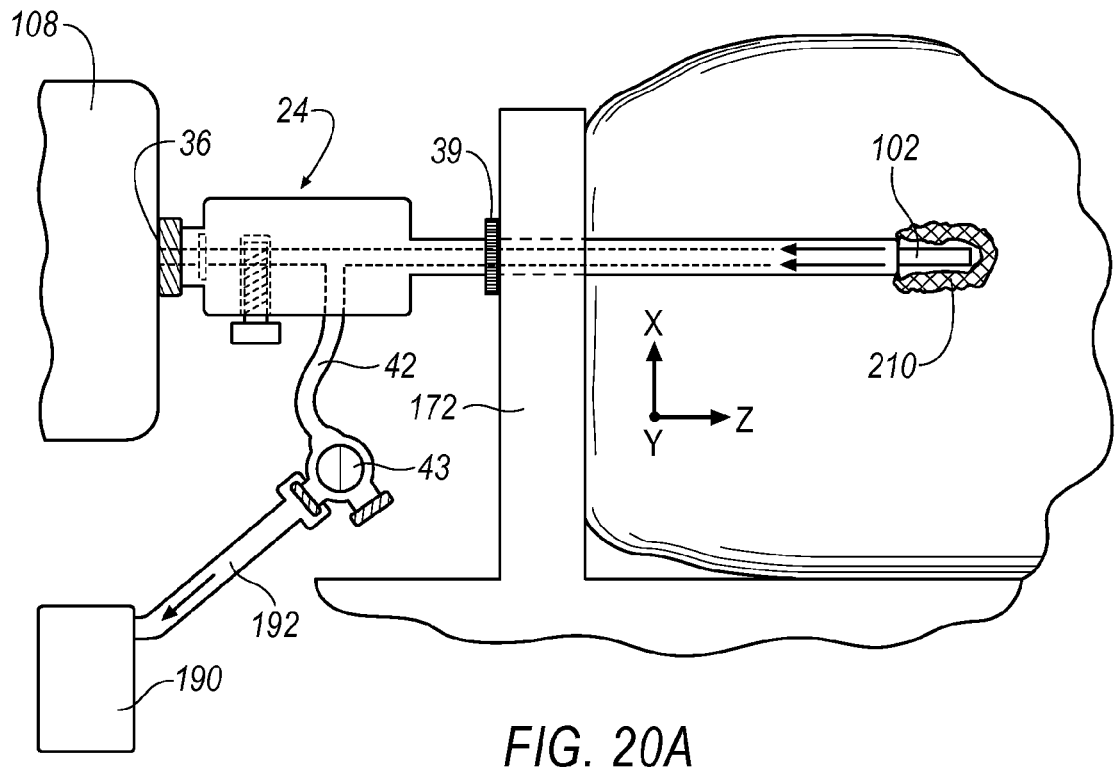
Figure 20B:
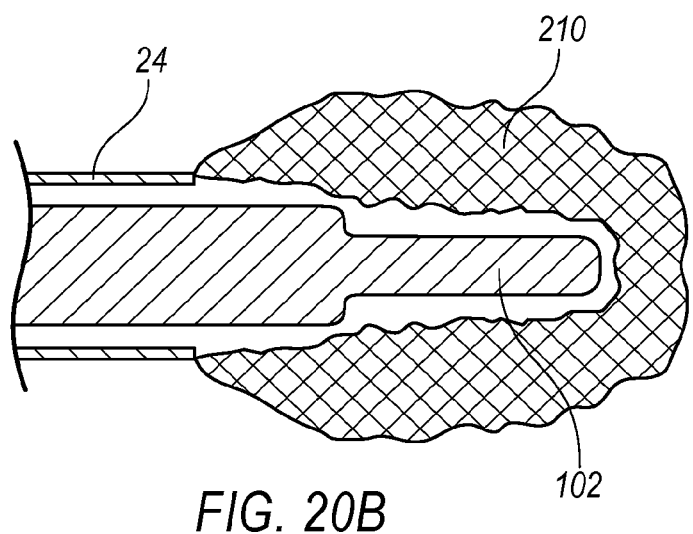
Figure 21:
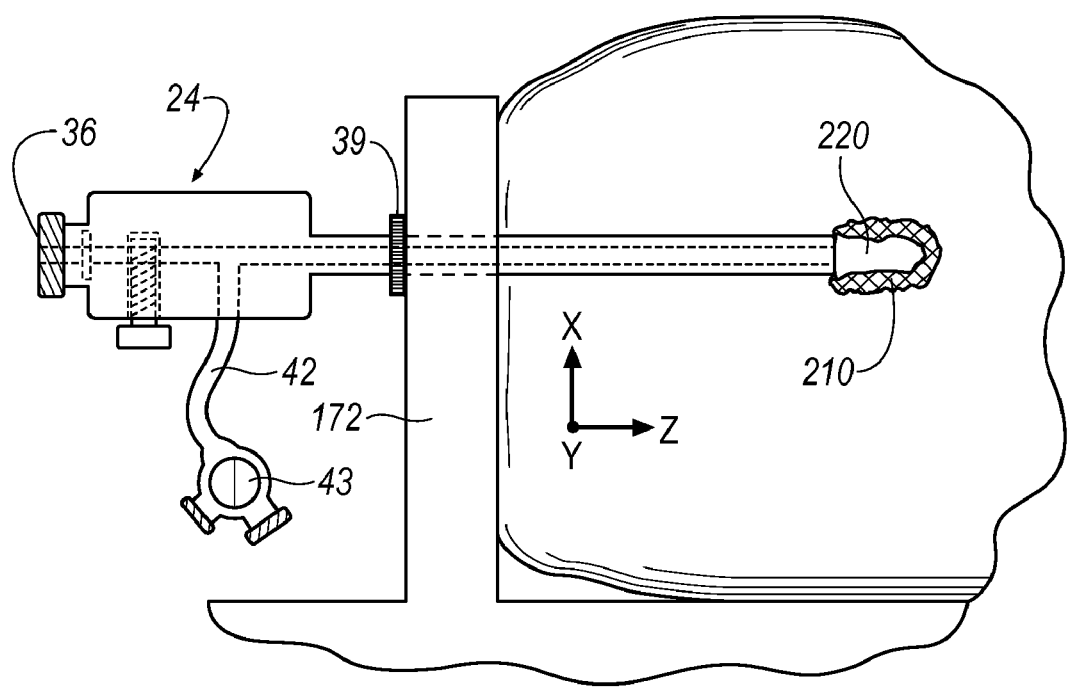

Once void 182 has collapsed under the vacuum, treatment tip 102, 102', 102", 102'", is activated (see FIG. 20A). The resulting damage to the surrounding tissue creates a margin 210 of ablated tissue that results in an increased success rate for treatment. FIG. 20B illustrates in detail margin 210 surrounding treatment tip 102, 102', 102", 102'" after the adjuvant treatment has been applied. The cells in margin 210 have been ablated and no longer pose a threat of continued growth of cancerous cells that may have been interstially surrounding target tissue 80.

After the adjuvant treatment has been applied, the surgeon may remove treatment device 100, 100', 100", 100'". Depending upon the type of adjuvant treatment applied through treatment tip 102, 102', 102", 102'", a post-treatment void may remain even after treatment device 100, 100', 100", 100'" is removed from patient's body 170. The surgeon may then review margin 210 under a preferred imaging modality. If, for example, it is determined that the margin is not correctly positioned or the adjuvant treatment has not achieved the appropriate margin 210, treatment may be continued by applying the adjuvant treatment repeatedly until medical imaging satisfactorily verifies the margin. Alternatively, margin 210 may be improved by repeating the procedure or a portion of the procedure beginning from any step. Further, the procedure may be repeated a predetermined number of times in order to reach an effective margin depth or shape.

After completion of the procedure, void 182 may be aspirated using wand 68. During or after aspiration, if any aspiration is desired, a final image of margin 210 may be taken to confirm removal of target tissue 80. The imaging also provides a record of the ablation zone for further analysis. Finally, an MRI identifiable treatment site marker, a collagen plug, or other medical treatment may be inserted into the biopsy site through outer cannula 24.

Among other features, the medical system of the present invention localizes the target site in a manner that provides for confirmation of the target site under MRI or other visualization modality, and allows positioning of a resection device to ensure the cutting element of the resection device can be accurately placed at the target site. Further, the medical system provides for accurate positioning of an adjuvant therapy device. Additionally, the system provides for verification of a margin created by an adjunctive therapy.

The medical system of the present invention also reduces side effects related to cancer treatments. Because the system uses accurate targeted treatment of the target site, the overall time of treatment is significantly reduced as compared with traditional radiation therapy. Further, there is no widespread exposure to radiation.

While the method is preferably suited for treatment of cancerous tissues that are unifocal, the treatment apparatus and method described herein may be used for any type of treatment including, but not limited to, multifocal diseases.

Figure 22:
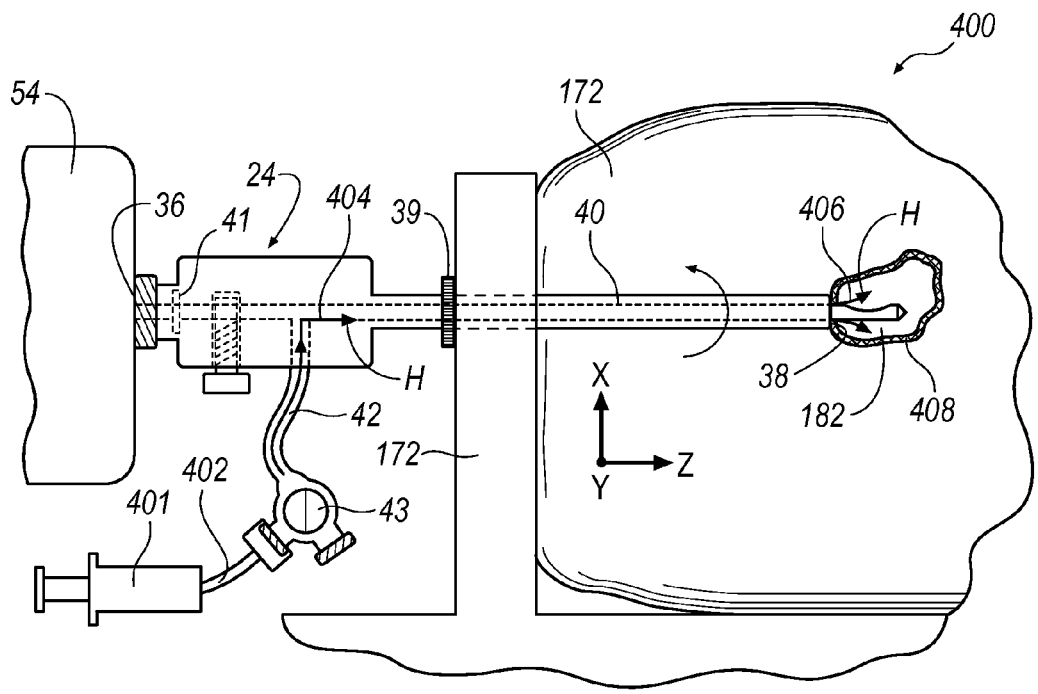
FIG. 22 is a haemostatic agent embodiment that introduces a haemostatic agent to a target site, according to an embodiment.

FIG. 22 shows a haemostatic agent embodiment 400 that introduces a haemostatic agent (represented by arrow(s) H) to target site 182 through valve 43 and fluid conduit 43. A syringe 401 (or other suitable applicator) is attached via a connecting tube 402 to fluid conduit 42. Haemostatic agent H is transported along a lumen 404 formed between outer cannula 56 and inner lumen 40 of outer cannula 24. Check valve 41 functions to prevent haemostatic agent H from exiting outer cannula 24 at proximal end 36. Haemostatic agent H is then deployed at 406 to target site 182 topically, e.g., haemostatic agent H is applied to a surface of target site 182. Once haemostatic agent H is deployed at 406, a haemostatic region 408 is formed that reduces, or in some cases, prevents bleeding into target site 182. Alternatively, haemostatic agent H may be introduced to target site 182 through an introducer, a side port, through a lumen, or through a resection device or treatment device itself.

In controlling the bleeding at target site 182, the effectiveness and efficiency of therapies delivered to target site 182 are improved. In general, the unknown insulative properties of bleeding are controlled such that a more precise, predictable, and reliable treatment results. In one example, cryogenic probe 102 (described in detail above with respect to FIGS. 7-9 and 19A-21) is used to ablate tissue surrounding target site 182. However, the efficiency of the ablation procedure depends significantly on the rate and quantity of energy transfer between probe 102 and the surrounding tissue. Where no haemostatic agent H is applied before ablation, target site 182 will continually bleed after resection apparatus 50 is removed. Thus, when probe 102 is inserted to perform the ablation procedure, the blood at target site 182 will become coagulated or hardened when exposed to probe 102. This may present a serious problem in an ablation procedure because coagulated blood behaves as an insulator between probe 102 and the surrounding tissues (see FIG. 19B). Due to the insulative properties of the blood, less energy transfer is performed between probe 102 and the surrounding tissue. The result is that the ablation procedure is less effective and margin 210 (see FIG. 20B) is reduced.

Other alternative uses for deploying haemostatic agent H include clotting a free flowing bleeder, e.g. to control significant blood loss. Moreover, stopping or reducing blood flow allows for heated and freezing adjuvant therapies to be applied with reduced heat sink effect from flowing blood that carries away heat or cold. In addition, haemostatic agent H may be used to dilute or flush out fluids that may be congregated near target site 182 while at the same time providing control for bleeding.

With the deployment of haemostatic agent H to target site 182, blood does not flow from the walls of target site 182. The result is improved performance from an ablation procedure using probe 102. By reducing or preventing bleeding from the surrounding tissue, the efficiency of the ablation procedure is improved resulting in an improved margin 210 (i.e., ablation of margin 210 in its entirety, or at least a greater depth of ablation than would have been possible if blood were present around probe 102).

Figure 23:
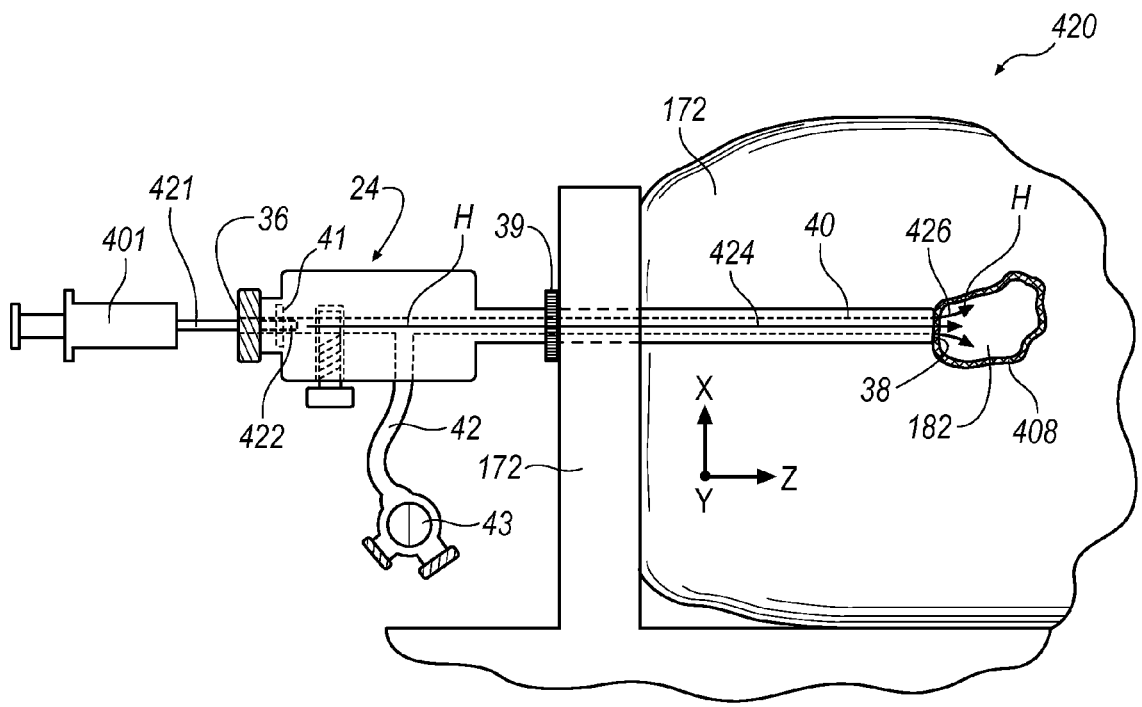
FIG. 23 is an alternative haemostatic agent embodiment to the embodiment of FIG. 22 that introduces a haemostatic agent to a target site.

FIG. 23 shows an alternative haemostatic agent embodiment 420 introducing a haemostatic agent H to target site 182 through proximal end 36 and valve 41. In this embodiment, handpiece 54 is removed from outer cannula 24 and thus, inner lumen 40 is unrestricted (See FIG. 2). Here, syringe 401 is inserted through proximal end 36 and valve 41 such that haemostatic agent H is deployed directly down inner lumen 40 along path 424 (See also FIG. 2). When reaching distal end 38 of outer cannula 24, haemostatic agent H is deployed at 426 to target site 182. In so doing, haemostatic region 408 is formed on an inner wall of target site 182. Depending upon the type and/or form of haemostatic agent H used, selection of a haemostatic deployment embodiment may be selected. For example, a liquid haemostatic agent H may perform well using either the embodiment of FIG. 22 or FIG. 23. However, a dry haemostatic agent H (e.g., a powder) may have improved deployment performance using the embodiment of FIG. 23. In so doing, the dry agent may be mixed with air and 'blown' into target site 182 by a mixture of powdered haemostatic agent H and air.

Figure 24:
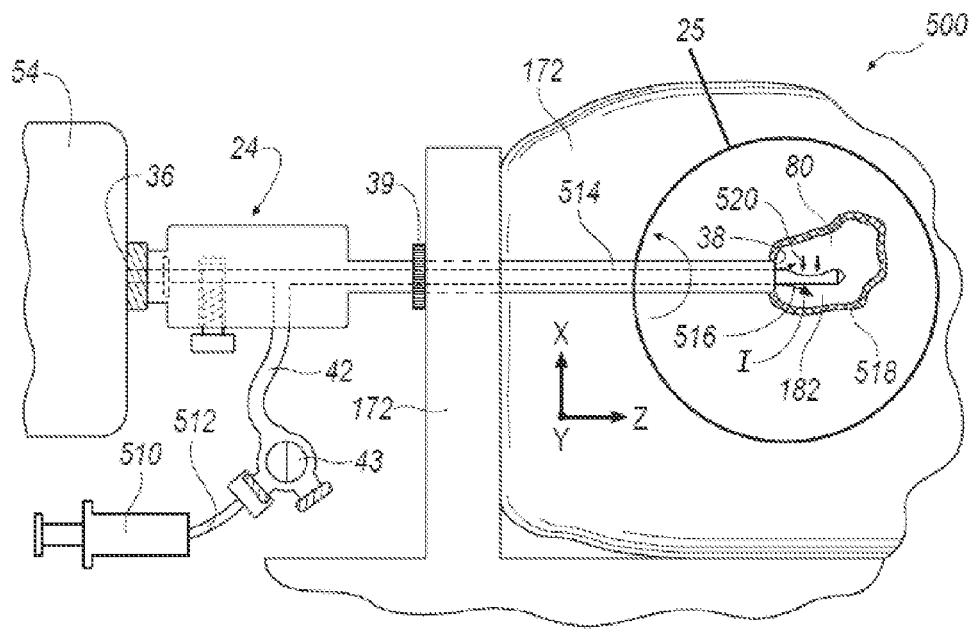
FIG. 24 is a procedure introducing an inking agent to a target site, according to an embodiment.

FIG. 24 shows a procedure 500 introducing an inking agent (represented by arrows I) to target site 182 through valve 43 and fluid conduit 42. An inking syringe 510 includes inking agent I, e.g. methylene blue, that pervades tissue and marks it for later visualization. In the case of methylene blue, inked tissue is, for at least a predetermined time period, semi-permanently marked by coloration. Thus, a surgeon may easily and directly identify the marked tissue when excised from target site 182. Stains other than methylene blue may be selected, including, for example, bismarck brown, carmine, coomassie blue, ethidium bromide, nile blue, or rhodamine. The selection of stain will primarily depend on the type of tissue targeted for stain and the method of observation, e.g., direct visualization with natural light, indirect visualization, visualization with ultraviolet light, etc.

Figure 25:
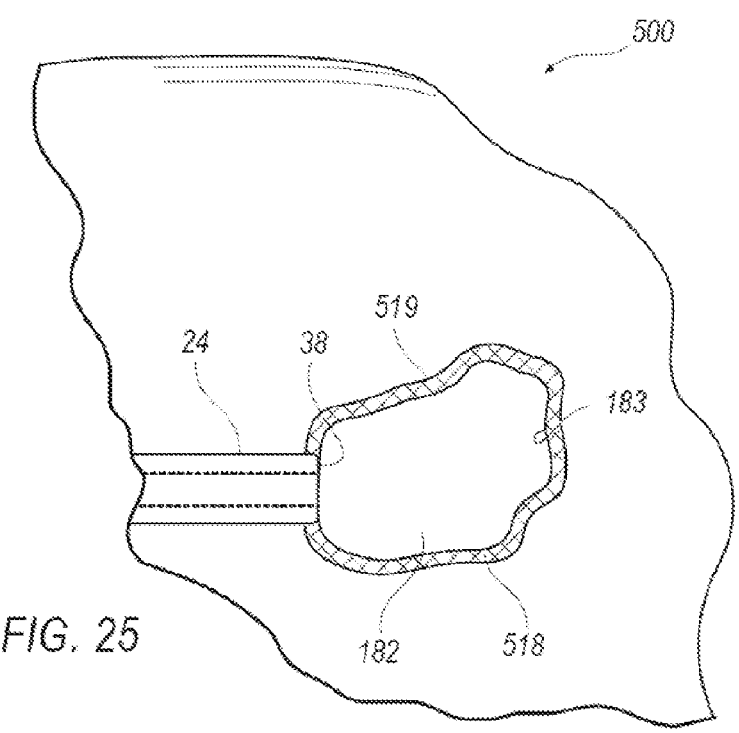
FIG. 25 is an inked margin region around the periphery of a target site.

FIG. 25 shows an inked margin region 518 around the periphery of target site 182 with outer cannula 24 removed. A boundary 519 defines a depth of inked margin region 518, which is dependent upon the type of inking substance used. For example, methylene blue may be used as an inking substance and will penetrate the tissue surrounding target site 182 at least a millimeter from the surface. The depth of penetration of the inking substance also may depend upon a number of factors including the tissue type, the dilution of the inking substance, the presence of bleeding at target site 182, etc.

Referring to FIGS. 26-28 and 30, inking and resection of tissue is discussed. A pathologist uses the resected tissue to verify the margin is a clear margin or a clean margin, e.g., the margin tissue does not contain cellular material that is considered pathologically diseased and/or cancerous. An inked portion of tissue, and particularly, partially inked portion 541 (described below) is used wherein the inked side indicates to the pathologist that the inking is on the side closest to the aggressively resected area. Thus, the pathologist knows that the inked portion is more likely to contain cancerous material, if any.

Figure 26:
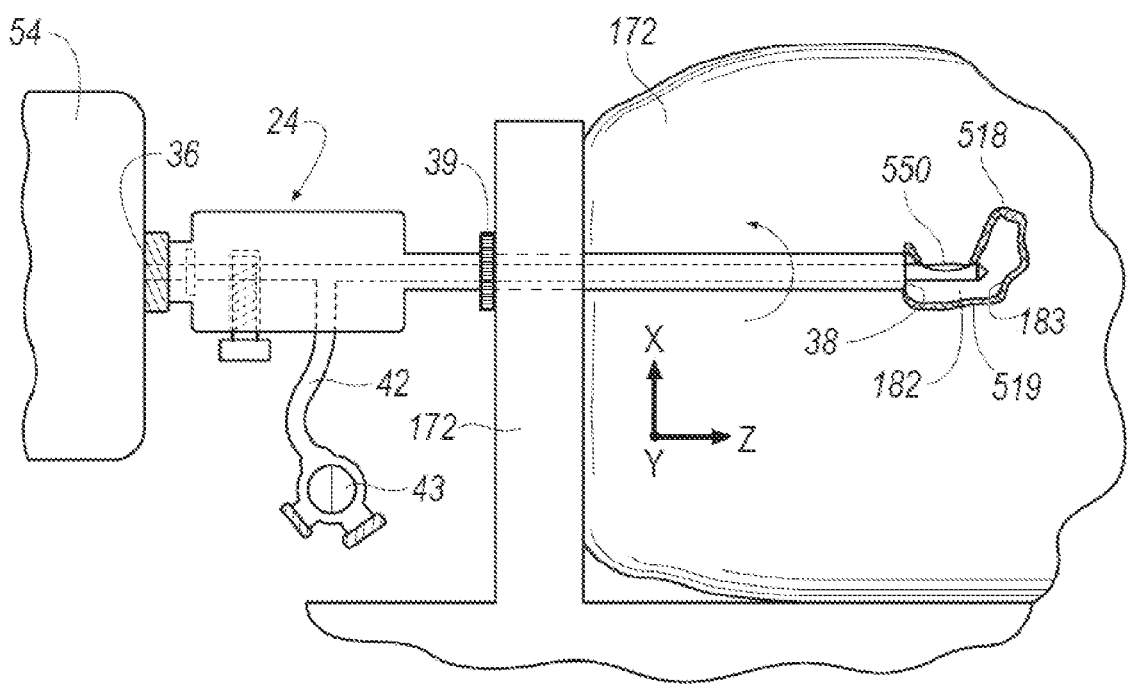
FIG. 26 is a resection of a target site including an inked margin region.

FIG. 26 shows further resection of target site 182, including inked margin region 518. A vacuum is drawn (see FIGS. 15-17) and tissue is resected from target region 182 as a prolapsed section 550 of tissue enters the cutting region. Thus, resection apparatus 50 is taking further tissue from target site 182 into inked margin region 518. As tissue is resected, it is subsequently collected in a collection canister such as, for example, a system as described in U.S. patent application Ser. No. 11/132,034, entitled "Selectively Openable Tissue Filter," filed May 18, 2005, to Joseph L. Mark et al., which is herein incorporated by reference in its entirety. Thus, when inked margin region 518 is resected, the tissue is held for inspection by the surgeon and pathologist.

Figure 27A:
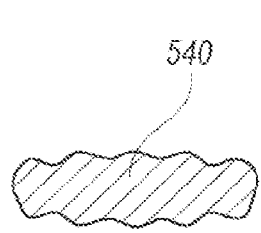
FIG. 27A is a fully inked portion of resected tissue.

FIG. 27A shows a fully inked portion 540 of resected tissue. As shown, the entire portion of tissue resected is inked with inking agent I. Thus, when viewed by the surgeon, it is known that the resected fully inked portion 540 is taken from inked margin region 518.

Figure 27B:
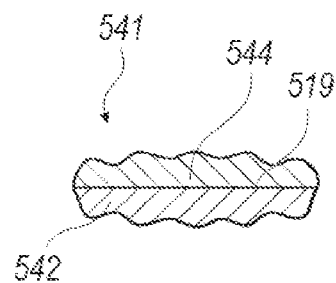
FIG. 27B is a partially inked portion of resected tissue.

FIG. 27B shows a partially inked portion 541 of resected tissue that includes an inked portion 542 and a non-inked portion 544. As shown, half of the resected tissue is inked while the other half is non-inked. When performing tissue resection, the surgeon may conclude from this portion of tissue that inked margin region 518 is being resected through the thickness inking. Thus, resection of inked margin region 518 is being visually identified and verified through the collection of resected tissue once a pathologist has confirmed that the sampled tissue, e.g. inked margin region 518, does not contain cancerous cells.

Figure 27C:
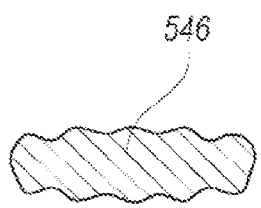
FIG. 27C is a fully non-inked portion of resected tissue.

FIG. 27C shows a fully non-inked portion 546 of resected tissue.

Figure 28:
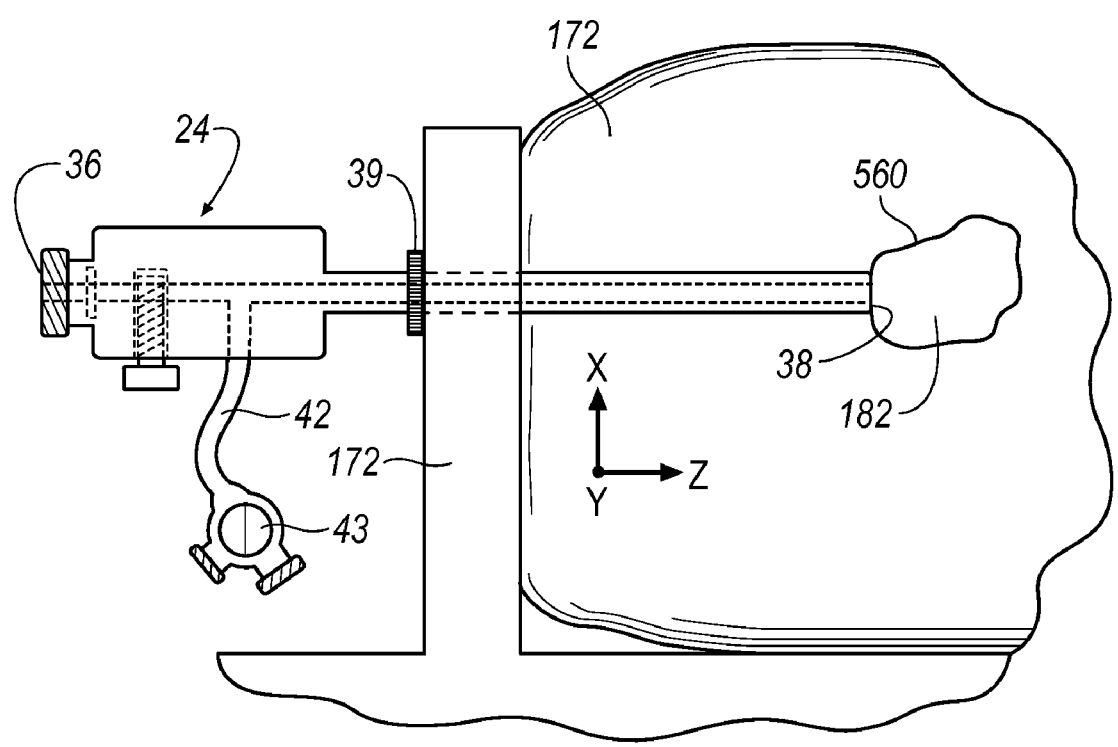
FIG. 28 is a target site after inking and resection to remove an inked margin region.

FIG. 28 shows target site 182 after inking and resection to remove inked margin region 518 (see FIG. 26). After tissue has been resected to an extent such that no inked tissue remains within target site 182, the margin is achieved, and a margined cavity 560 remains.

Figure 29:
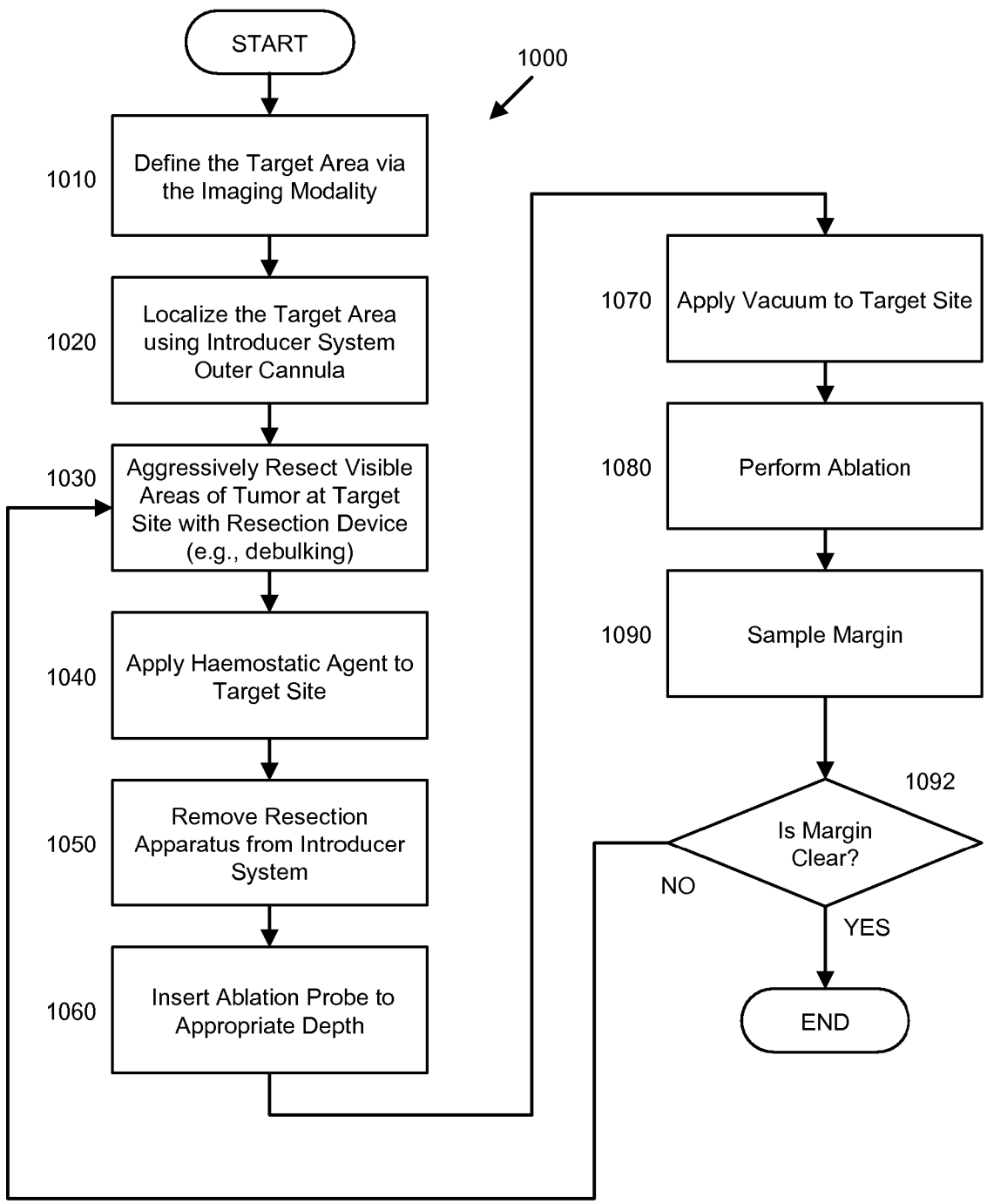
FIG. 29 is a flow diagram of a resection process, including application of a haemostatic agent as is described above with respect to FIGS. 22 and 23.

FIG. 29 is a flow diagram of a resection process 1000, including application of haemostatic agent H (see FIGS. 22-23) as is described above with respect to FIGS. 22 and 23. Resection process 1000 is used with inking methods described herein to confirm with pathology that significant margins have been realized and that no cancerous cells are detected within the margin region. Moreover, using the inking process, a pathologist is able to determine which side of the resected tissue was positioned inward toward target site 182. Resection process 1000 starts at step 1010 wherein the target site 182 is defined via the imaging modality. The imaging modality chosen provides an image of general target area 610 (such as in FIG. 33 wherein a lesion 620 is apparent within general target area 610). In this way, the surgeon has a visual image of general target area 610 and can decide on a course of action for access and treatment. Control then proceeds to step 1020.

At step 1020, general target area 610 is localized using introducer system outer cannula 24 (explained below in detail with respect to FIG. 31 and steps 1910 through 1940). In general, the surgeon inserts and positions outer cannula 24. Thereafter, the surgeon selectively inserts distal end 46 of target confirmation device 26 to determine the position of outer cannula 24 with respect to general target area 610. Using the imaging modality, the surgeon may be provided real-time guidance (in the case of ultrasound imaging) or selective snapshots (in the case of MRI). In any case, the image provided by the imaging modality is used to localize outer cannula 24 such that treatment is appropriately positioned with respect to general target area 610. In a final step, the surgeon confirms the position of outer cannula 24 with respect to general target area 610 (explained above in detail with respect to FIGS. 12-14 and localization of target tissue 80). Control then proceeds to step 1030.

At step 1030, tissue is aggressively resected at visible areas of the tumor at target site 182 using resection apparatus 50 (discussed in detail with respect to FIG. 16). Ideally, the resection operation will remove the entirety of any remaining lesion tissue. However, in many circumstances, resection of a lesion carries the risk that not all of the lesion tissue will be resected. Control then proceeds to step 1040.

At step 1040, haemostatic agent H is applied to target site 182 (discussed above in detail with respect to FIGS. 22 and 23). Haemostatic agent H prevents or otherwise reduces the amount of bleeding in target site 182 (see FIGS. 22-23). With haemostatic agent H applied, film 408 reduces bleeding and prevents target site 182 from accumulating bodily fluids, including blood. Such a reduction in fluid collection improves the efficiency of secondary treatments to target site 182. Control then proceeds to step 1050.

At step 1050, resection apparatus 50 is removed from outer cannula 24 (see FIG. 17). Note that step 1050 may also be performed before step 1040. Control then proceeds to step 1060.

At step 1060, treatment tip 102 is inserted to the appropriate depth to target site 182 through outer cannula 24 (see FIG. 18). It is important to note that the therapy need not be provided by treatment device 100 (See FIG. 7). For example, treatment may be provided by cryoprobe 102' (see FIGS. 7-9), light therapy 102" (see FIG. 10), or electro 102''' (see FIG. 11). Further, as described below, treatment provided through outer cannula 24 may include for example external beam HIFU therapy, interstitial HIFU therapy, electroporation therapy, ultrasonicporation therapy, or interstitial microwave therapy. Control then proceeds to step 1070.

At step 1070, a vacuum is applied to target site 182 via outer cannula 24 (see particularly FIGS. 19A and 19B). This process is described in detail above with respect to FIGS. 18-21. In addition to the vacuum being applied to pull tissue close to treatment tip 102, where haemostatic agent H is applied to target site 182, greater collapse of the cavity in a uniform manner will be realized because target site 182 is better sealed due to reduced bleeding. Control then proceeds to step 1080.

At step 1080, treatment tip 102 is energized and ablation occurs within target site 182 (discussed above in detail with respect to FIGS. 20A and 20B). Using haemostatic agent H, less blood will be present, and/or coagulated, at target site 182. Thus, blood is not available as an insulator around treatment tip 102. Therefore, more energy is transferred to the surrounding tissue and is more concentrated at margin region 518. Control then proceeds to step 1090.

At step 1090, target site 182 is inked and tissue is resected using a quadrant approach. That is to say, when using an aperture-based resection device, the aperture is rotated such that samples are taken in quadrants. In another example, the aperture may be rotated at twelve (10) o'clock, three (3) o'clock, six (6) o'clock, and nine (9) o'clock. In this way, multiple samples are taken from target site 182 at the margin. Control then proceeds to step 1092.

At step 1092, the resected tissue is then verified by pathology that the inked portions do not include cancerous tissue. If cancerous tissues are found in the resected tissue, control then proceeds to step 1030 and aggressive resection may begin again with further treatment required. If cancerous tissue is not found in the resected tissue, e.g. the margin is clear, resection process 1000 then ends.

Figure 30:
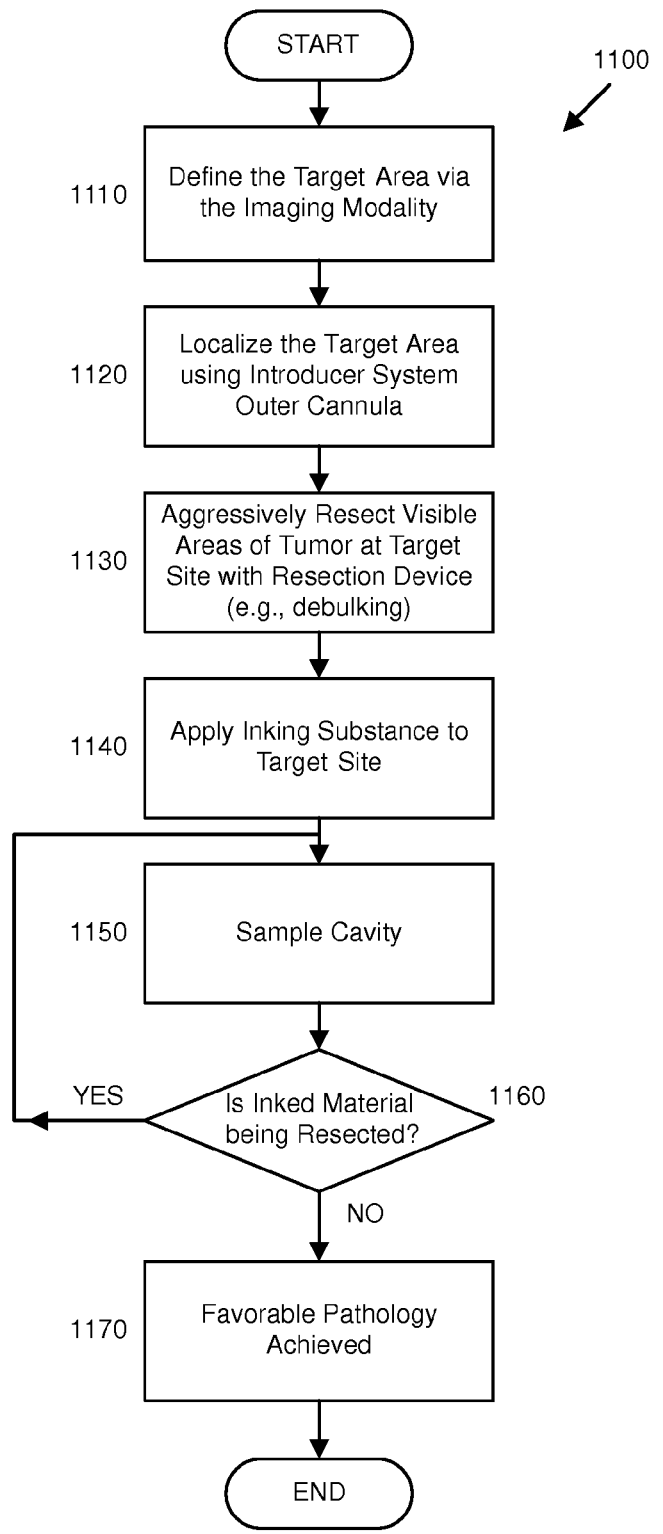
FIG. 30 is a margin process for determining whether a margin region has been resected, and is related to FIGS. 24-28.

FIG. 30 shows a margin process 1100 for determining whether margin region 518 has been resected (see FIGS. 24-28 for detailed descriptions of margins resection). Margin process 1100 begins at step 1110 where target site 182 is defined via the imaging modality. In this way, the image guided therapy allows a surgeon to determine the success or thoroughness of the treatment at any stage, to determine that more treatment is necessary, or that treatment is complete. Control then proceeds to step 1120.

At step 1120, general target area 610 is localized using introducer system outer cannula 24 (explained below in detail with respect to FIG. 31 and steps 1910 through 1940). In general, the surgeon inserts and positions outer cannula 24. Thereafter, the surgeon selectively inserts distal end 46 of target confirmation device 26 to determine the position of outer cannula 24 with respect to general target area 610. Using the imaging modality, the surgeon may be provided real-time guidance (in the case of ultrasound imaging) or selective snapshots (in the case of MRI). In any case, the image provided by the imaging modality is used to localize outer cannula 24 such that treatment is appropriately positioned with respect to general target area 610. In a final step, the surgeon confirms the position of outer cannula 24 with respect to general target area 610 (explained above in detail with respect to FIGS. 12-14 and localization of target tissue 80). Control then proceeds to step 1130.

At step 1130, tissue is aggressively resected at visible areas of the tumor at target site 182 using resection apparatus 50 (discussed in detail with respect to FIG. 16). Ideally, the resection operation will remove the entirety of any remaining lesion tissue. However, in many circumstances, resection of a lesion carries the risk that not all of the lesion tissue will be resected. Control then proceeds to step 1140.

At step 1140, haemostatic agent H is applied to target site 182 (discussed above in detail with respect to FIGS. 22 and 23). Haemostatic agent H prevents or otherwise reduces the amount of bleeding in target site 182 (see FIGS. 22-23). With haemostatic agent H applied, film 408 reduces bleeding and prevents target site 182 from accumulating bodily fluids, including blood. Such a reduction in fluid collection improves the efficiency of secondary treatments to target site 182. Control then proceeds to step 1150.

At step 1150, the cavity at target site 182 is sampled. Using resection apparatus 50, samples of tissue are resected from inked margin region 518 and collected in a collection canister (or other suitable filter or containment apparatus). At this time, the surgeon checks the resected tissue to determine what type of tissue is being resected, and can distinguish between the location of the resected tissue as it was taken from inked margin region 518. For example, a surgeon may see fully inked portion 540, partially inked portion 541, fully non-inked portion 546, or a mixture thereof (see FIGS. 27A-27C) in the collection canister. When, for example, the resected tissue conforms substantially with fully inked portion 540, the surgeon knows that inked margin region 518 is in the process of being resected. When, for example, the resected tissue conforms substantially to partially inked portion 541, the surgeon knows inked margin region 518 is close to being fully consumed in the area that tissue-receiving opening 60 is exposed to at target site 182 (See FIG. 4). Additionally, for example, when the resected tissue appears like fully non-inked portion 546, then the surgeon knows that inked margin region 518 is substantially removed at the location where tissue-receiving opening 60 is exposed.

It is also important to note, that tissue-receiving opening 60 may be rotated and translated about distal end 38 of outer cannula 24, such that the full extent of margin region 518 is resected (see FIGS. 15-17). Otherwise, for example, were a surgeon to leave resection apparatus 50 in a fixed position (necessarily providing that tissue-receiving opening 60 is in a fixed position), only prolapsed region 550 would be resected and the remainder of inked margin region 518 would remain. Control then proceeds to step 1160.

At step 1160, a check is performed to determine whether inked tissue is still being resected. The surgeon observes the resected tissue for tissue marking resembling fully inked portion 540, partially inked portion 541, and fully non-inked portion 546 (see FIGS. 27A-27C). If the resected tissue resembles fully inked portion 540 and/or partially inked portion 541, then the surgeon can infer that inked margin region 518 is still at least partially intact and that more resection is necessary. On the other hand, if the tissue resected fully or substantially resembles fully non-inked portion 546, then the surgeon can infer that inked margin region 518 has been removed and that only margined cavity 560 remains (see FIG. 28). However, it is important to note that the determination that only margined cavity 560 remains should be inferred where the surgeon has rotated tissue-receiving opening 60 and sampled at various areas of inked margin region 518 to ensure that not only a portion of inked margin region 518 has been sampled. If inked tissue is still being resected, control proceeds to step 1150. Otherwise, control then proceeds to step 1170.

At step 1170, a favorable pathology has been achieved as indicated by the lack of inked tissue being resected. At this point, inked margin region 518 is removed and margined cavity 560 has been created. Thus, the margin has been achieved through a method of inking a cavity, resecting the cavity tissue, and determining whether the inked tissue has been removed. Margin process 1100 then ends.

As an alternative to using inks, contrast agents may also be used in therapy delivery and treatment. In one example, nanoparticles may be used to highlight cancerous cells in large scale including tumors and masses, using a selected imaging modality such that the therapy may be image guided and/or image verified (explained in detail with respect to FIGS. 29-36). For example, magnetic resonance imaging can be used with contrast agents including monocrystalline iron oxide nanoparticles (MIONs). The MIONs are in brief, iron oxide superparamagnetic nanoparticles that are encased in dextran. In an enhanced mode, cross-linked iron oxide nanoparticles (CLIOs) may be used. In use, molecules such as transferin may be attached to MIONs and CLIOs such that the molecules "home-in" on cells (e.g., selectively target cells) having higher than normal metabolic activity. In this way, the MIONs and CLIOs accumulate in the cancerous cells. Then, under magnetic resonance imaging, the cancerous cells and tumors may be identified by an increased imaging response. In another example, ferumoxtran-10 may be used as a nanoparticle contrast agent for magnetic resonance imaging.

Additionally, smart contrast agents may be employed that have special properties in that they are not detectable using magnetic resonance imaging until they have reached the target site. In one example, smart agents may encapsulate gadolinium within the delivery molecule and protect the gadolinium from water protons rendering the gadolinium effectively inert to magnetic resonance imaging. When the intended target (an enzyme or cellular ion) interacts with the delivery module, the interaction between water and gadolinium is allowed, resulting in changes in T1 relaxation that can be detected by magnetic resonance imaging. One example of a smart contrast agent is EgadMe (EgadMe being a chelated gadolinium caged by a galactopyranose molecule). EgadMe allows interaction of water with the caged gadolinium when EgadMe comes in contact with a β-galactosidase enzyme.

Beyond gadolinium, which may only remain in tissue for approximately thirty minutes, longer lasting contrast agents such as ferumoxtran-10 may be preferred in that they may allow multiple imaging sequences and treatment with a single dose. Gadolinium agents may require multiple doses during a procedure and may also give false readings due to new lesions created by the treatment due to traumatized tissue (e.g., additional doses of gadolinium agents may seek out lesions created by treatment rather than cancerous cells). On the other hand, ferumoxtran-10 allows an iron particle to enter a cell and the imaging is not degraded by additional doses or treatment related trauma. Depending upon the situations at hand, longer lasting contrast agents or gadolinium may be preferred depending upon the particular advantages associated with use.

Figure 31:
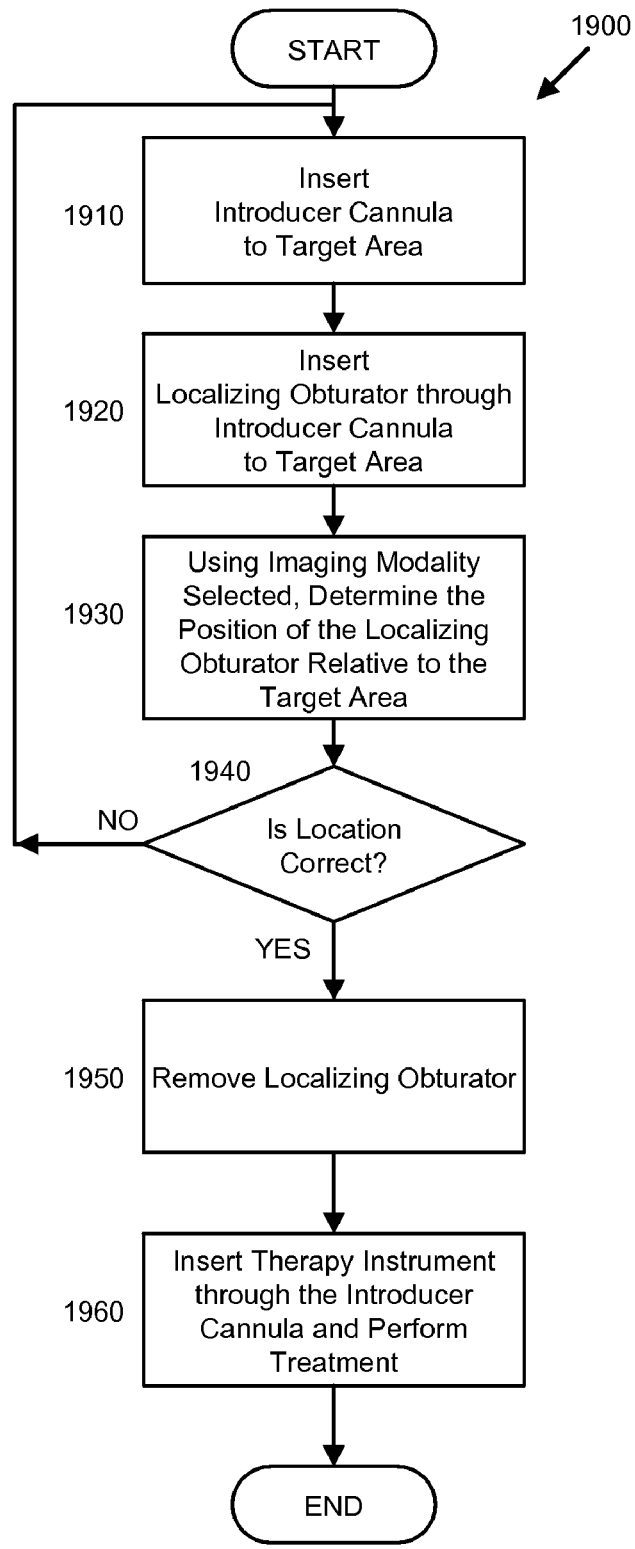
FIG. 31 is a contrast agent localization process wherein contrast agents are used in conjunction with imaging modalities and a target confirmation device to verify therapy positioning.
Figure 32:
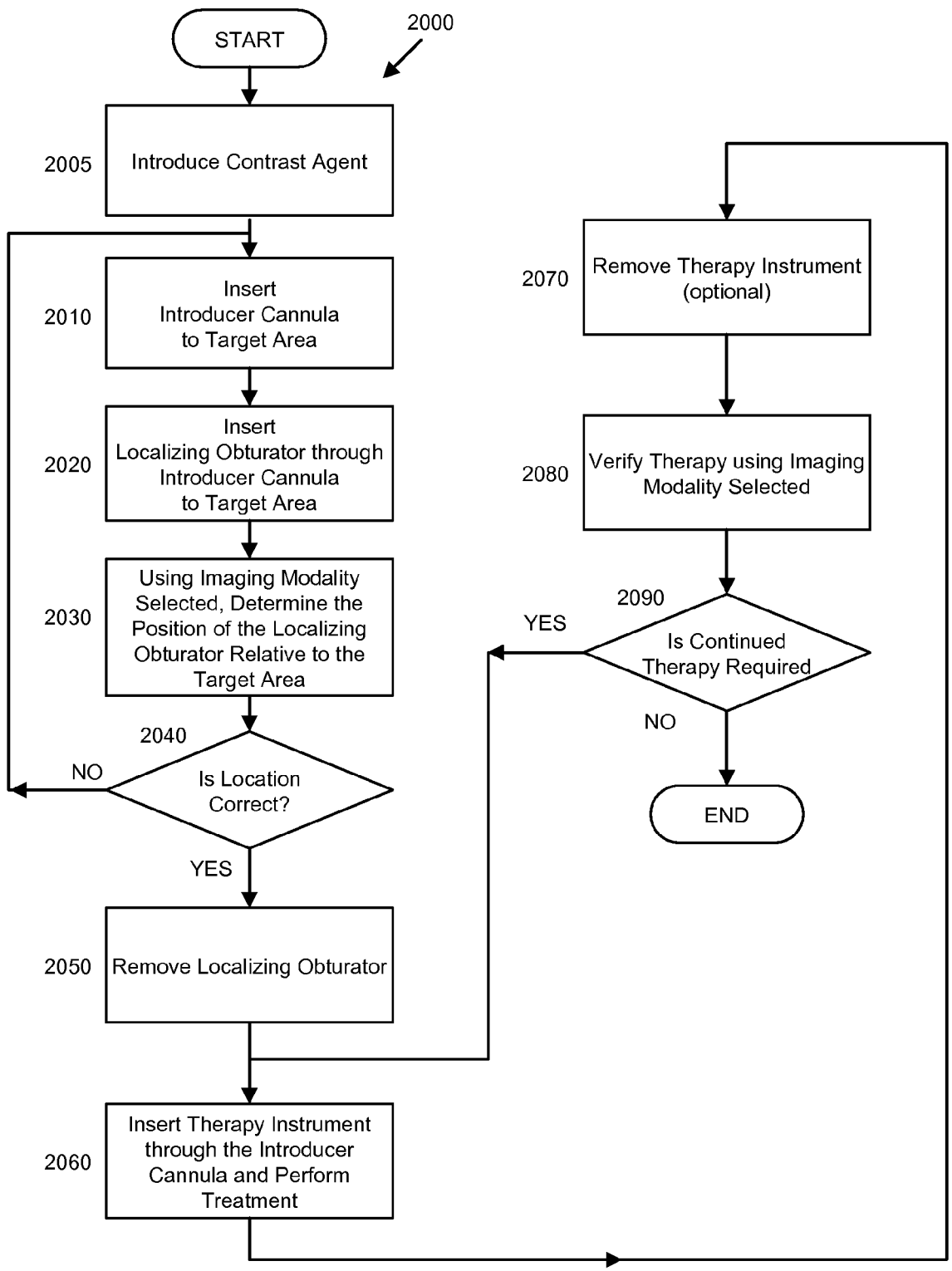
FIG. 32 is a contrast agent therapy verification process wherein a lesion is identified, treatment is performed, and treatment is verified using a selected imaging modality.

Moving now to image directed therapy and image guided localization, FIGS. 31 and 32 show processes that include image directed therapy and image guided localization. FIGS. 33-36 show certain steps of these procedures and should be reviewed in concert with FIGS. 31 and 32.

FIG. 31 shows a contrast agent localization process 1900 wherein contrast agents are used in conjunction with imaging modalities and target confirmation device 26 to verify therapy positioning. Using the imaging modality, e.g., MRI, PET, CT, ultrasound, terahertz technologies, etc., the location of lesion 620 is more particularly determined with the use of a contrast agent. Moreover, combinations of imaging modalities may be used together. In so doing, the location of outer cannula 24 is precisely determined such that therapy may be delivered accurately. Because contrast agents are not present where tissue has already been resected, i.e. there is no agent in an empty space created by a cavity, target confirmation device 26 may be used to localize lesion 620. Moreover, even where a contrast agent was applied to the margins of lesion 620, tissue resection may have removed the contrasted portions of the cavity wall. Contrast agent localization process 1900 begins at step 1905 where a contrast agent is introduced to general target area 610 and allowed to associate with lesion 620. Control then proceeds to step 1910.

At step 1910, outer cannula 24 is inserted within general target area 610 in an attempt to locate target 48' centrally within lesion 620. Generally, an introducer cannula, e.g. outer cannula 24, may be inserted to an approximate location and may then be further inserted, pulled back, or re-directed as required by contrast agent localization process 1900. Control then proceeds to step 1920.

Figure 33:
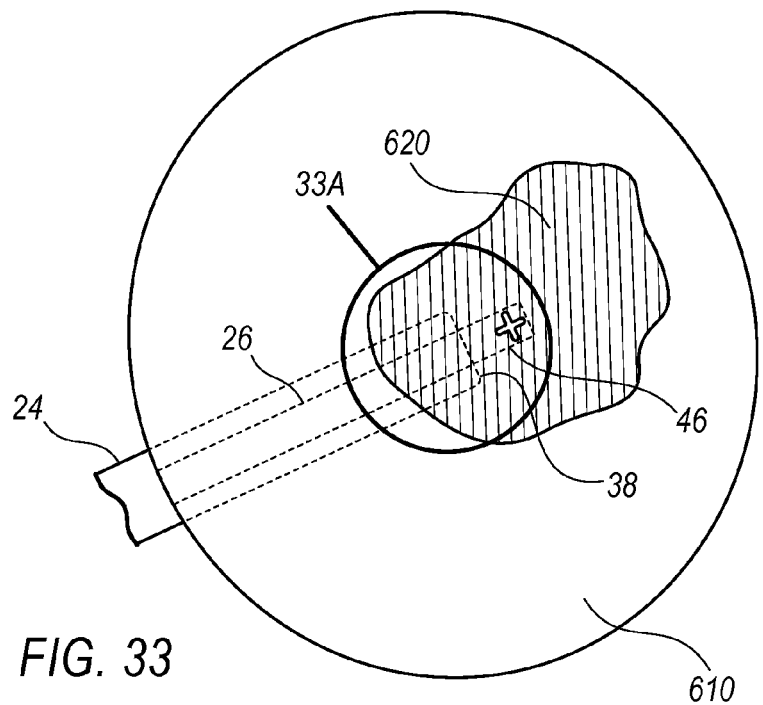
FIG. 33 is an attempt to position an outer cannula centrally with respect to a lesion.
Figure 34:
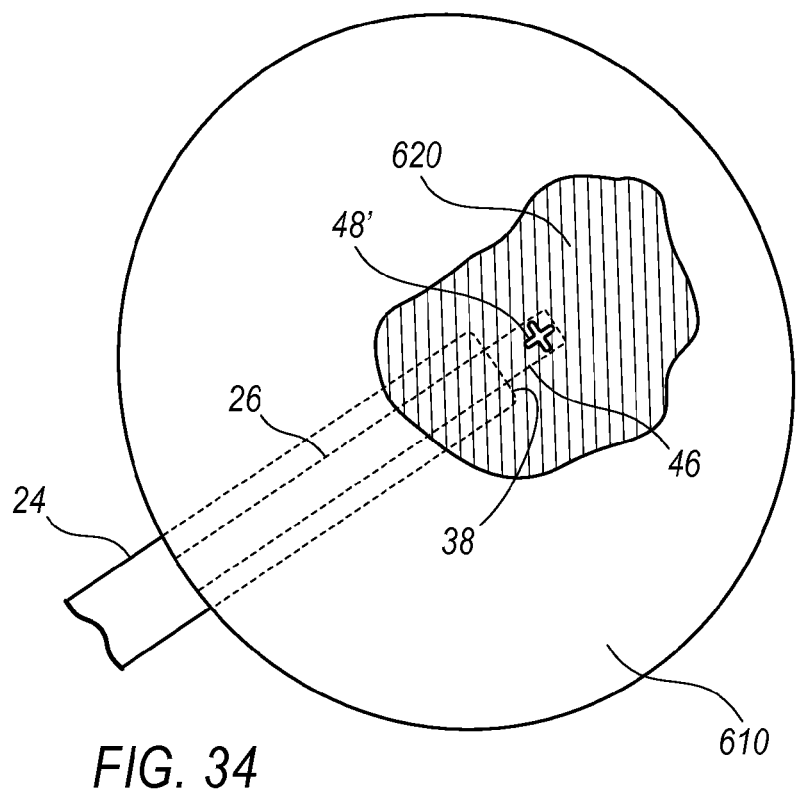
FIG. 34 is a center-of-mass placement of a target.

At step 1920, target confirmation device 26 is inserted through outer cannula 24 to lesion 620 (see FIGS. 14, 33 and 34). Target confirmation device 26 (described in detail above with respect to FIGS. 3, 3A, 3B, and 14) is selected such that it is visible under the chosen imaging modality. Control then proceeds to step 1930.

At step 1930, the selected imaging modality, in conjunction with an appropriate contrast agent, is used to determine whether target confirmation device 26 is in the correct position. In an embodiment, a nanotechnology contrast agent is used to emphasize lesion 620 such that a lesion becomes apparent in the imaging modality chosen. Control then proceeds to step 1940.

At step 1940, the position of target confirmation device 26, also viewable under the imaging modality, is then compared with lesion 620 that is emphasized with the contrast agent. Using the contrast agent and target confirmation device 26, the position of lesion 620 as well as the position of target confirmation device 26 is enhanced and may be more easily determined. If outer cannula 24 is correctly positioned, e.g. target confirmation device 26 is centrally located within lesion 620, then control proceeds to step 1950. Otherwise, control proceeds to step 1910 where outer cannula 24 is repositioned.

At step 1950, target confirmation device 26 is removed from outer cannula 24. Control then proceeds to step 1960.

At step 1960, a therapy instrument is inserted through outer cannula 24 to lesion 620 and therapy is performed (see FIGS. 15-21). It is important to note that the therapy delivered may be the therapies described above including, but not limited to, resection, ablation (including electrode, photonic, and cryogenic ablation), delivery of therapeutic agents, margin determinations, HIFU therapy, electroporation therapy, ultrasonicporation therapy, interstitial microwave therapy, and any combination thereof. By particularly locating lesion 620 using a contrast agent, target confirmation device 26 may be precisely positioned to lesion 620 or to the centralized mass of diseased tissue such that delivery of the therapy is more precise. Further, contrast agent localization process 1900 may be used multiple times in the same clinical session if more than one target site has been identified or where more target sites are further identified during the session through the use of a contrast agent. In this way, the specific location of lesion 620 is found and therapy is delivered precisely. Contrast agent localization process 1900 ends.

FIG. 32 shows a contrast agent therapy verification process 2000 wherein lesion 620 is identified, treatment is performed, and treatment is verified using a selected imaging modality. At least in the case of FIG. 32, the therapy instrument is not limited to the specific embodiments of treatment device 100 but may also include the resection of tissue. Contrast agent therapy verification process 2000 begins at step 2005 where a contrast agent is introduced to general target area 610 and allowed to associate with lesion 620. Control then proceeds to step 2010.

At step 2010, outer cannula 24 is inserted to lesion 620. Generally, an introducer cannula, e.g. outer cannula 24, may be inserted to an approximate location and may then be further inserted, pulled back, or re-directed as required by contrast agent therapy verification process 2000. Control then proceeds to step 2020.

At step 2020, target confirmation device 26 is inserted through outer cannula 24 to lesion 620. Target confirmation device 26 (described in detail above with respect to FIGS. 3, 3A, 3B, and 14) is selected such that it is visible under the chosen imaging modality. Control then proceeds to step 2030.

At step 2030, the selected imaging modality, in conjunction with an appropriate contrast agent, is used to determine whether target confirmation device 26 is in the correct position. In an embodiment, a nanotechnology contrast agent is used to emphasize lesion 620 such that a lesion becomes apparent in the imaging modality chosen. Control then proceeds to step 2040.

At step 2040, the position of target confirmation device 26, also viewable under the imaging modality, is then compared with lesion 620 that is emphasized with the contrast agent. Using the contrast agent and target confirmation device 26, the position of lesion 620 as well as the position of target confirmation device 26, are enhanced and may be more easily determined. If a localizing obturator is correctly positioned, e.g. target confirmation device 26 is centrally located within lesion 620, then control proceeds to step 2050. Otherwise, control proceeds to step 2010 where outer cannula 24 is repositioned.

At step 2050, target confirmation device 26 is removed from outer cannula 24. Control then proceeds to step 2060.

At step 2060, treatment device 100 is inserted through outer cannula 24 to lesion 620 and therapy is performed. For more detail, see FIGS. 9, 15-21, and 35. Control then proceeds to step 2070.

Figure 35:
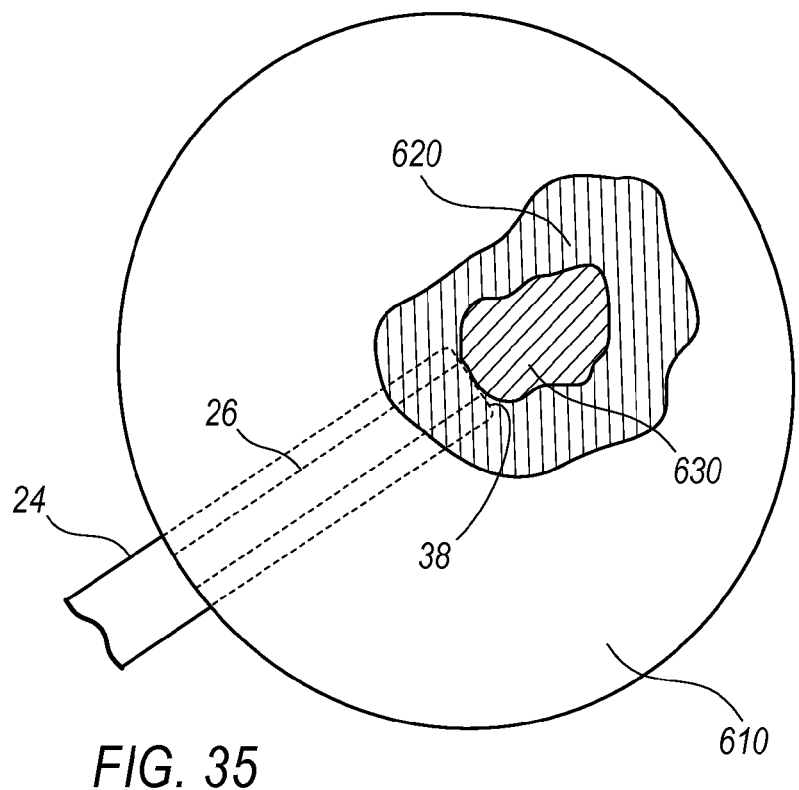
FIG. 35 is a partially treated region within a lesion.

At step 2070, treatment device 100 may be removed; see also FIG. 35. Depending upon the type of therapy being performed and the imaging modality selected, the removal of the therapy instrument may be required for step 2080. However, some therapies, such as delivered therapeutics, may not require removal of the therapy instrument. Control then proceeds to step 2080.

At step 2080, the delivered therapy is verified using the imaging modality selected; see also FIG. 35. In one example, cryoablation is verified where the ablated area, that originally had been highlighted with the contrast agent, is now a signal void. In general, and when using a contrast agent to confirm therapy, an adjuvant therapy destroys tissue at least one (1) millimeter beyond the resected cavity wall. Thus, image verified therapy can test to detect whether an adjuvant treatment has destroyed tissue that contained marking agents or inking agents. By directly observing the results of therapy, extent of the ablation, the completeness of treatment may be determined. In another example where the therapy includes resection, the extent of resection may be directly determined. After substantial resection has taken place, the extent of resection of the tissues highlighted by the contrast agent can be visualized to directly determine whether all of the contrast agent has been removed. In this way, the surgeon determines whether more resection is necessary (e.g., if contrast enhanced regions still exist after resection) or whether the resection was complete (e.g., where no highlighted regions still exist at target site 182). Control then proceeds to step 2090.

At step 2090, a determination is made as to whether continued therapy is required. If continued therapy is required, control proceeds to step 2060. Otherwise contrast agent therapy verification process 2000 ends.

FIG. 33 shows a first attempt to position outer cannula 24 centrally with respect to lesion 620. Using distal end 46 of a localizing obturator, the location of outer cannula 24 relative to lesion 620 is precisely determined. Generally, the object of positioning outer cannula 24 is to place distal end 38 centrally within lesion 620 such that improved tissue section and improved delivery of adjuvant therapy is accomplished. However, a surgeon may desire distal end 38 in any location that treatment is desired. In this instance, distal end 38 is desired to be placed centrally to lesion 620 such that lesion 620 may be debulked or treated.

The placement of target 48' to lesion 620 in FIG. 33 shows a missed placement attempt. This is determined when lesion 620, outer cannula 24, and target 48' are imaged. When lesion 620 is missed or the surgeon determines a different position is necessary, outer cannula 24 is repositioned. For example, such repositioning may occur as described in detail above with respect to FIG. 29, step 1020; FIG. 30, step 1120; FIG. 31, steps 1910-1940; and FIG. 32, steps 2010-2040.

Before target 48' is correctly positioned, e.g., in the position that treatment is desired, a number of image guidance verification steps and subsequent repositioning of outer cannula 24 may be required. Where magnetic resonance is chosen as the imaging modality, the patient is moved inside the bore to image and moved outside the bore for repositioning of outer cannula 24 as well as treatment. The patient may be subsequently placed back in the bore for further imaging to confirm location and treatment.

Alternatively, a real-time guidance approach may be taken when, for example, ultrasound is chosen as the imaging modality. In this case, the surgeon sees the placement target 48' while locating outer cannula 24, for example, when distal end 46 includes features of a stylet such as a trocar tip.

Figure 33A:
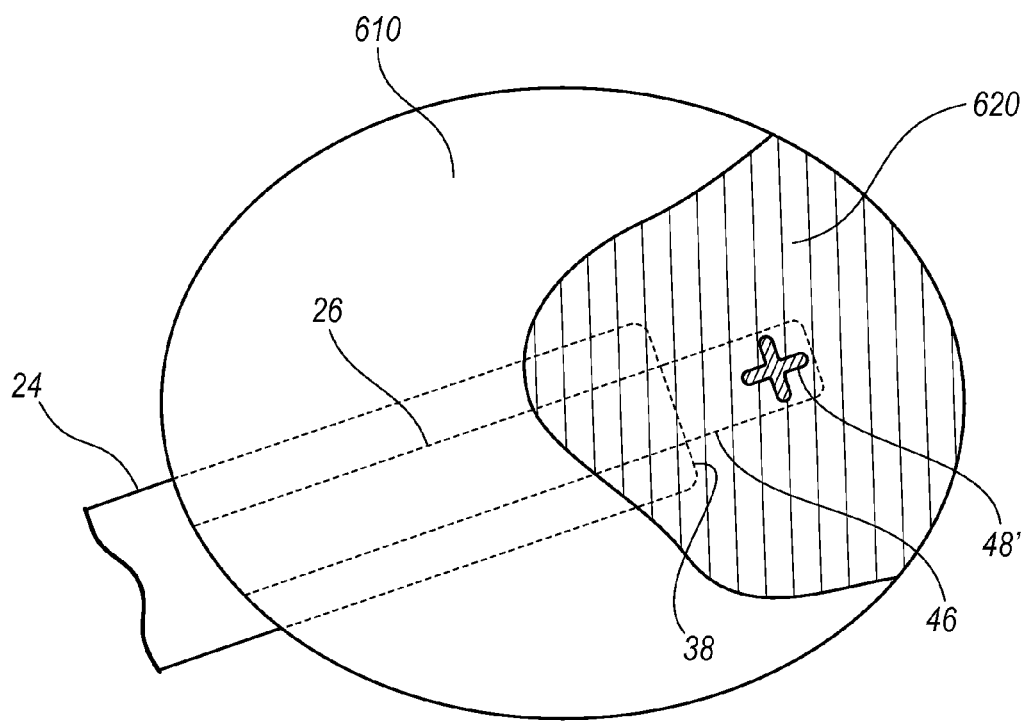
FIG. 33A is a portion of FIG. 33 that has been enlarged to show the positioning attempt.

FIG. 33A shows a portion of FIG. 33 in greater detail. Target 48' is cross-shaped for easy identification (e.g., the cross-shape is quickly recognizable because it is not a natural anatomical shape). Further, target 48' may be a material that is recognizable to the imaging modality being used. Additionally, target 48' may contain a contrast agent that provides greater response to the imaging modality than normal tissue. This allows the location of target 48' to be quickly and accurately determined.

Alternatively, target 48' may provide a signal void when used with certain imaging modalities (e.g., MRI). In this case, target 48' will appear as a dark cross in the image. This is helpful for identification purposes when, for example, lesion 620 has been treated with a contrast agent. Thus, the identification of target 48' is improved where lesion 620 provides a high response and where target 48' appears as a signal void.

Target confirmation device 26 is used in these cases as a localizing obturator for outer cannula 24. Thus, the primary use of target confirmation device 26 is to confirm initially where resection apparatus 50 or an ablative device (e.g., electrode, photonic, and cryogenic ablation) will be placed relative to lesion 620, when the device is inserted through outer cannula 24. In other words, the use of target confirmation device 26 with an imaging modality confirms that treatment will be placed where it is intended. Further, the confirmation is performed using materials for outer cannula 24, target confirmation device 26, and target 48' that are friendly and usable with a selected imaging modality without distortion of artifact that would otherwise reduce the surgeon's ability to determine the location of target 48' relative to lesion 620.

FIG. 34 shows a center-of-mass placement of target 48'. In this case, placement of distal end 38 is confirmed by using an imaging modality to compare the location of target 48 and lesion 620. Once confirmed, the surgeon removes target confirmation device 26 from outer cannula 24 and inserts a therapy device, which may include a resection device. The confirmed position of outer cannula 24, and thus distal end 38, allows for precisely positioned therapy at lesion 620. Further, aggressive therapies may be employed because the position is known and confirmed. Thus, because the position of outer cannula 24 is confirmed using an imaging modality, it is known that the therapy will employed at lesion 620.

FIG. 35 shows a partially treated region 630 within lesion 620. At this stage, therapy has been applied near the center of lesion 620, resulting in partially treated region 630. As shown, the therapy device (used to delivery the therapy to lesion 620) has been removed for clarity. The therapies employed may include treatment by therapeutic agents, resection, or other therapies described herein. For detailed examples of therapy employment at lesion 620, see above FIGS. 9, 15-21; FIG. 29, step 1060; FIG. 30, step 1030; FIG. 31, step 1960; and FIG. 32, 2060.

Turning now to additional types of therapies, the methods disclosed herein are applicable to more than just electrode, photonic, and cryogenic ablation. For example, the methods disclosed herein may also be used with external beam high intensity focused ultrasound (HIFU), electroporation therapy, ultrasonicporation therapy, and interstitial microwave therapy. These therapies include the use of radiofrequency electrodes, microwave antennas, laser fiberoptics, and ultrasound transducers. Each of these therapy modalities may be provided in a minimally invasive manner.

External beam HIFU therapy includes a specialized ultrasound probe that is placed near lesion 620. The specialized ultrasound probe is deployed down outer cannula 24 and placed near lesion 620. The surgeon then views lesion 620 on an ultrasound monitor and maps the areas of concern based on the ultrasound image and possibly through the use of a targeted contrast agent. After the trouble regions are located and identified, the surgeon uses at high intensity ultrasound beam that is focused through the specialized ultrasound probe to the precise areas, e.g. lesion 620, that require treatment. The high intensity ultrasound beam generates high heat a the focused area that destroys the tissue in an ablative manner. Moreover, because the heat from external beam HIFU therapy is transmitted directly to the tissue, it is possible also to treat the tissue directly adjacent to lesion 620, and in this way, create a margin using the therapy process itself.

In an alternative treatment, electroporation therapy is a highly targeted method of delivering therapeutic drugs and/or compounds directly to cells. A specialized probe, typically having electrodes, is deployed along outer cannula 24 at lesion 620. By briefly applying an electric field to the cell, a hole opens in the cell wall temporarily. This temporary opening allows therapeutics to enter the cell, and afterwards, the cell wall closes. The opening and closing of the cell wall occurs without permanently damaging the cell. However, after therapy, the therapeutics delivered are now trapped within the cell and may kill the cell, if desired. This method is desirable for the treatment of tumor cells, wherein the tumor cells are treated with chemotherapeutic drug molecules. The nature of electroporation allows these drugs to enter the tumor cell, resulting in enhanced cytotoxic effects.

Alternatively, ultrasonicporation therapy is used which operates with similar principles to electroporation therapy, except that the probe uses ultrasonic energy to drive the therapeutic molecules. The driving effect increases absorption by the cells. The ultrasound energy also increases the depth and dispersion to which the therapeutics are delivered in lesion 620.

Moreover, interstitial microwave therapy may be deployed down outer cannula 24 for treating lesion 620. The interstitial microwave therapy device uses antennae to radiate microwave energy directly at a target site. Moreover, the interstitial microwave therapy may provide both thermal treatment (i.e., ablation through heating) as well as radiation therapy, depending upon the configuration of the probe and the transmitted frequencies.

Figure 36:
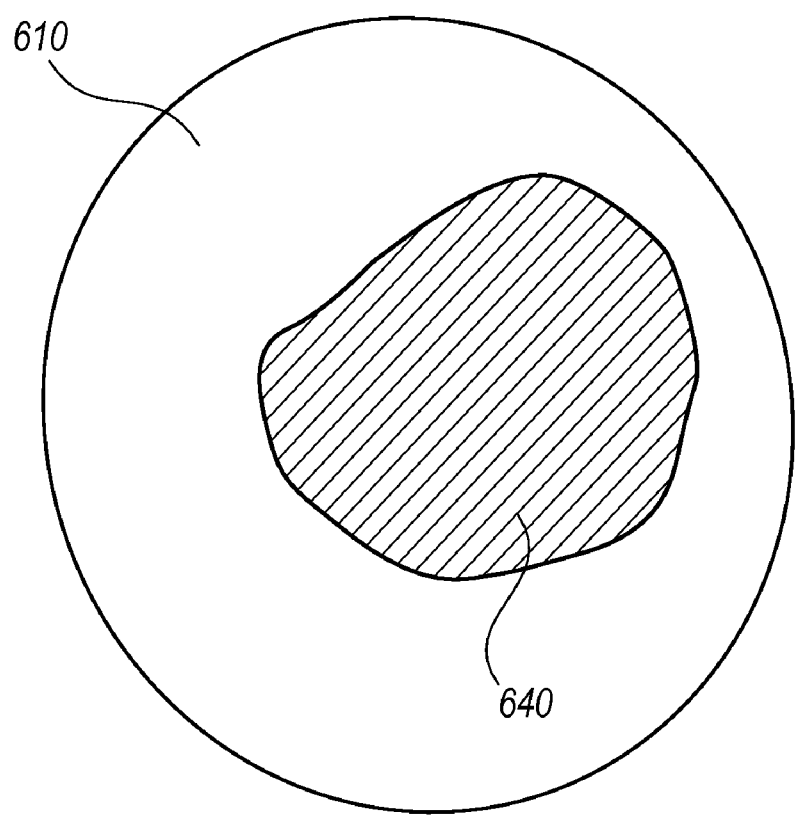
FIG. 36 is a completed region, after a lesion is fully treated.

FIG. 36 shows a completed region 640. At this phase, lesion 620 (from FIGS. 33-35) is fully treated, leaving completed region 640. An important advantage of the therapy approach described herein is a significant reduction in time to complete a therapy procedure. Lesion 620 is debulked (e.g., resected) to reduce the volume of the tumor. Next, an adjuvant therapy, such as one of the therapies listed herein, is applied to the debulked region to improve the success of the resection procedure. Generally, these adjuvant therapies would have been performed in a stand-alone process that consumes substantially more time than the procedures described herein. Further, these procedures are often limited in effectiveness and are very painful. Thus, the methods and apparatuses described herein reduce the time of the procedure, increase the effectiveness of adjuvant therapy delivered, and likely reduce the pain associated with adjuvant therapy at least because the amount of time and number of visits is reduced.

Figure 37:
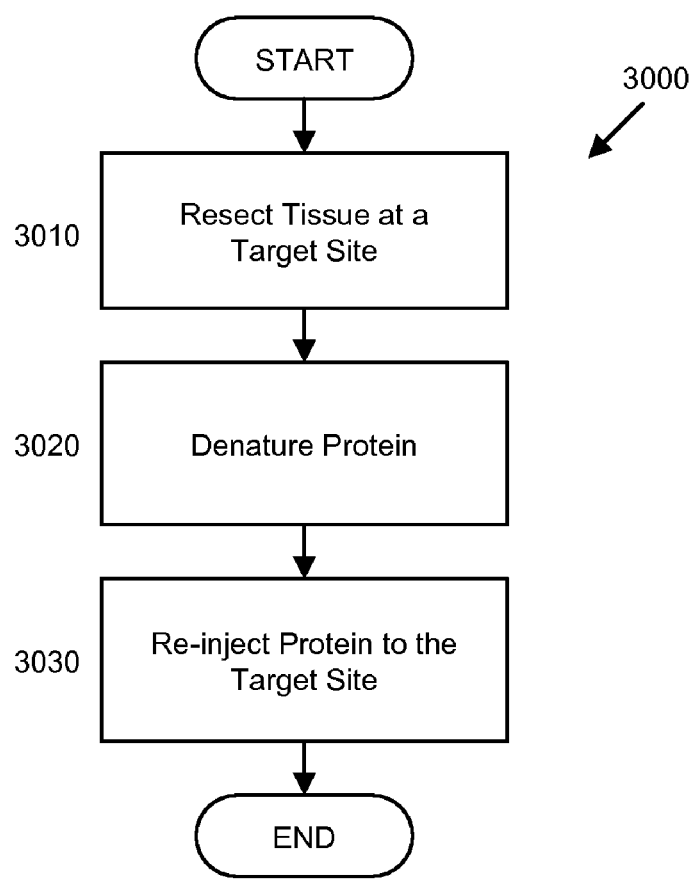
FIG. 37 is a re-injection process that provides for removal of cancerous tissue, denaturing the protein contained therein, and re-injecting the protein to stimulate the body's natural immune response against the cancerous cells.

In addition to the adjuvant treatments described above, it is also possible to resect tissue for modification and re-inject the modified tissue as a treatment. For example, resected tissue may be removed and converted to denatured protein. FIG. 37 shows a re-injection process 3000 that provides for removal of cancerous tissue, denaturing the protein contained therein, and re-injecting the protein to stimulate the body's natural immune response against the cancerous cells. Re-injection process 3000 begins at step 3010 where tissue is resected and received by a collection canister (or other suitable filter or containment apparatus). The process then continues at step 3020.

At step 3020 a specialist denatures the resected tissue. Denaturing typically comprises altering a protein by a physical or chemical agent to reduce or deactivate its biological activity. The process then continues at step 3030.

At step 3030 the denatured protein is re-injected into the patient at the target site. The denatured protein is no longer cancerous, but is foreign such that the body's immune system will respond. In this way, the denatured protein stimulates the body's immune system at the target site and provides that any cancerous cells that may be left over in the margin are targeted. In sum, the denatured protein is then re-injected to the site of resection to trigger an immune response by the patients' body that would further attack cancerous cells. Thus, the cancerous lesion is removed, modified, and replaced as a type of protein that triggers a natural immune response of the body that would then attack remaining cancerous cells, if any. This type of adjuvant treatment would further localize treatment to the location(s) that are most in need. Thus, whole-body treatments such as chemotherapy and radiation to destroy cancer cells would be reduced. Re-injection process 3000 then ends.

With respect to FIGS. 38-51, brachytherapy is introduced as an adjuvant treatment to ensure a margin is created after tissue resection. Moreover, the brachytherapy discussed herein may also be used with other adjuvant treatments (such as (resecting tissue, ablating tissue, heating tissue, freezing tissue, applying chemicals to tissue, external beam HIFU therapy, interstitial HIFU therapy, electroporation therapy, ultrasonicporation therapy, and interstitial microwave therapy, described herein). Additionally, the method that brachytherapy is delivered to a cavity may also be used in conjunction with a tissue marker where the delivery vessel (e.g., a radioactive seed) may also be used as a tissue marker.

Figure 38:
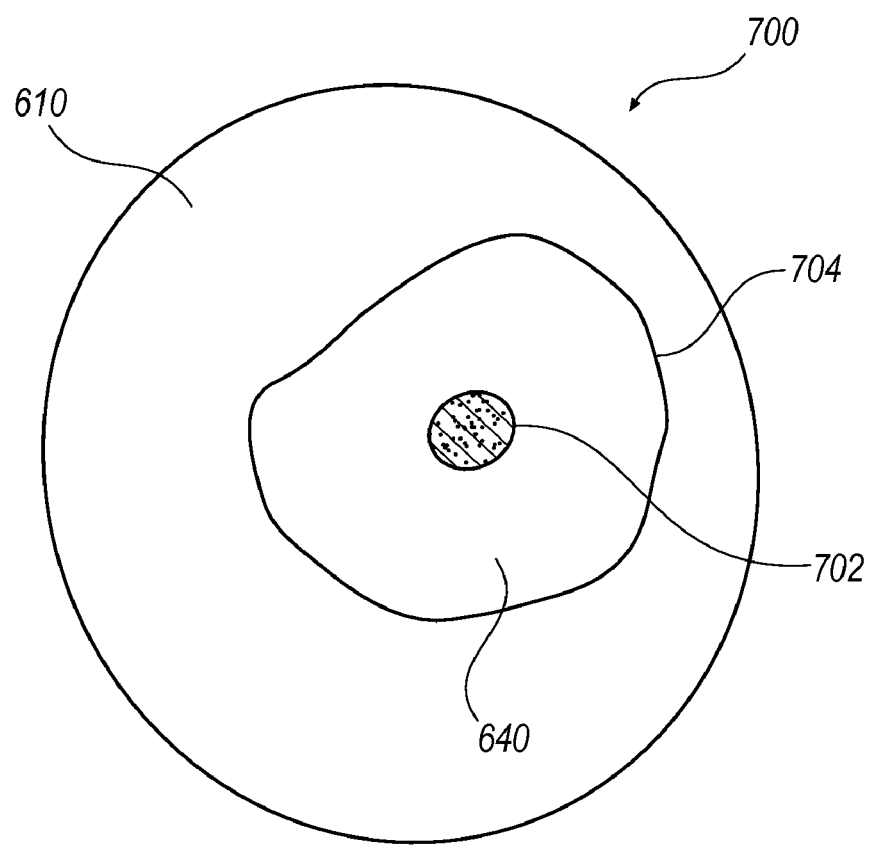
FIG. 38 shows placement of a localized treatment seed (e.g., brachytherapy)

FIG. 38 shows placement of a localized treatment seed 702 (e.g., brachytherapy) at target site 640. In general, treatment seed 702 is placed at target site 640 after tissue is resected. Thus, using the apparatuses and processes described herein, a cavity is formed. Treatment seed 702 is placed in the cavity after tissue resection to provide additional therapy directly at target site 640. In so doing, treatment seed 702 provides a high-dose of radiation, for example, to the surrounding margin 704 at the inner periphery of target site 640. Because treatment seed 702 is placed directly at target site 640, the majority of radiation is directed to the margin 704 rather than broadly exposing the surrounding healthy tissue.

Treatment seed 702 may be, for example, solid, sintered, or constructed as a binder material holding a radioactive agent. Alternatively, seed 702 may be a plastic seed that has been coated with a radioactive substance. Seed 702 may also have a powder glued to the surface to provide the treatment. Moreover, seed 702 may perform dual roles as a site marker that includes treatment material (e.g., radioactive material) to provide treatment at site 640.

Figure 39:
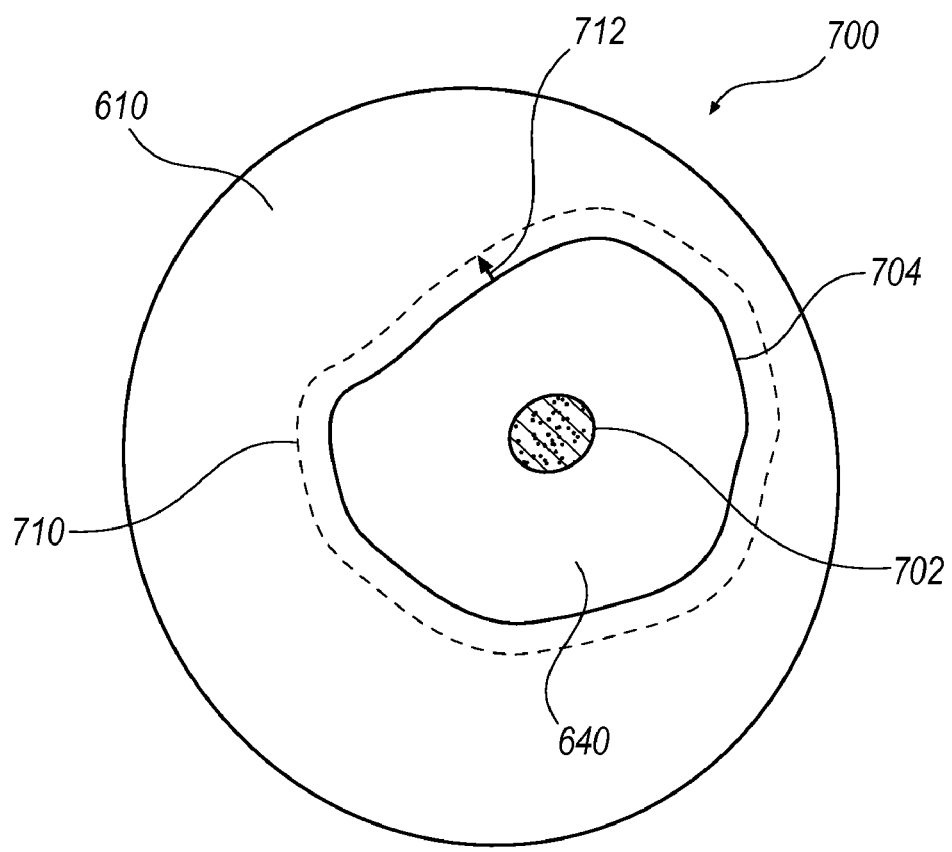
FIG. 39 shows a treatment penetrating the surrounding tissue using a single localized treatment seed.

FIG. 39 shows treatment from treatment seed 702 penetrating tissue 610 to a treatment region 710. Treatment seed 702 is, for example, a pellet containing a predetermined amount of I-125. Those skilled in the art will appreciate that the dose in time and the level of radioactivity of seed 702 is adjustable depending upon the radioactive source material and mass of said material included in seed 702. As FIG. 39 shows, seed 702 provides radiation (not shown) through tissue 610 to a predetermined depth 712. By providing the radiation directly to the tissue 610 surrounding target site 640, a margin 704 of target site 640 is treated. There is a greater chance that if cancer cells were to remain about margin 704, that the interstitial brachytherapy would apply treatment directly to the remaining cancerous cells and destroy them. Treatment region 710 generally follows the inner surface of target site 640 to predetermined depth 712.

Figure 40:
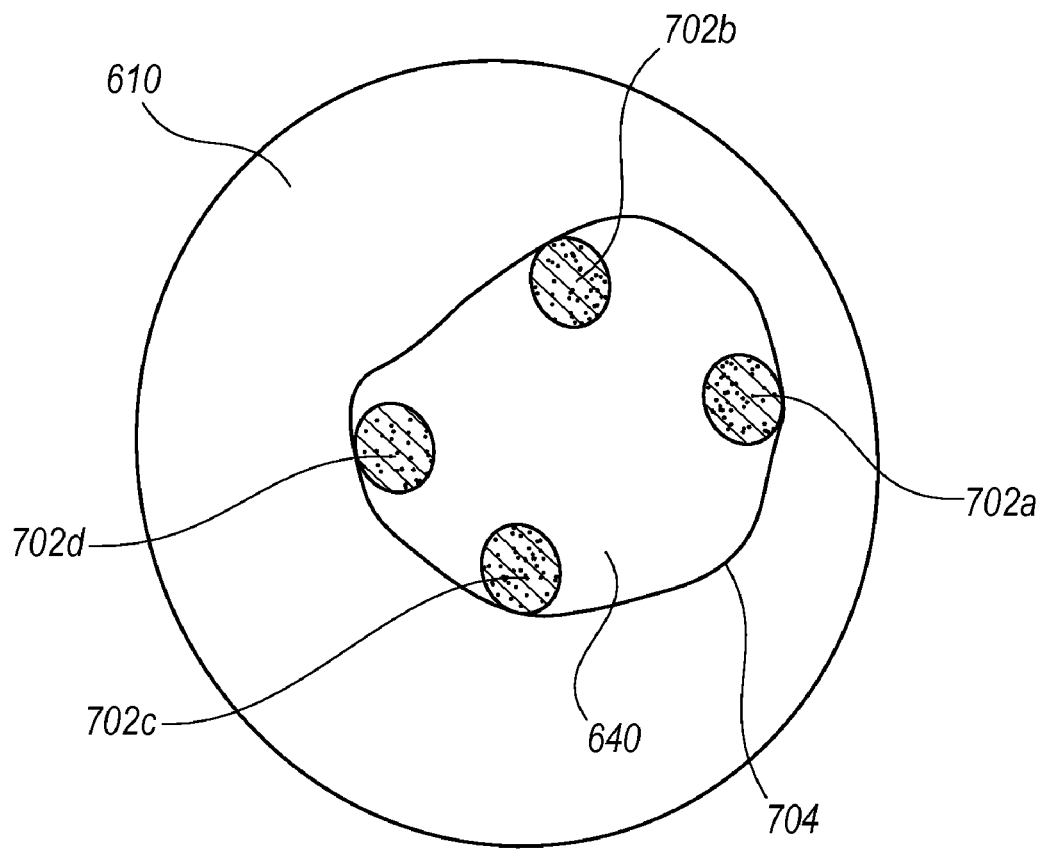
FIG. 40 shows placement of multiple treatment seeds at a target site.

FIG. 40 shows placement of multiple treatment seeds 702a, 702b, 702c, 702d at the inner periphery of target site 640. Multiple seeds 702a-702d provide an option for interstitial brachytherapy to add seeds having different properties, e.g. radioactivity, material, dose, etc. In so doing, for example, seed 702a may include a radioactive source that provides greater penetration into the tissue 610. Whereas, seed 702b may provide a longer-term dose, i.e. a longer time of release. Thus, each seed 702a-702d may be tailored to a specific goal of the interstitial brachytherapy such that each seed 702a-702d may have properties allowing a plurality of predetermined treatment therapy goals. Seeds 702a-702d are generally placed around the inside perimeter of targets site 640.

Figure 41:
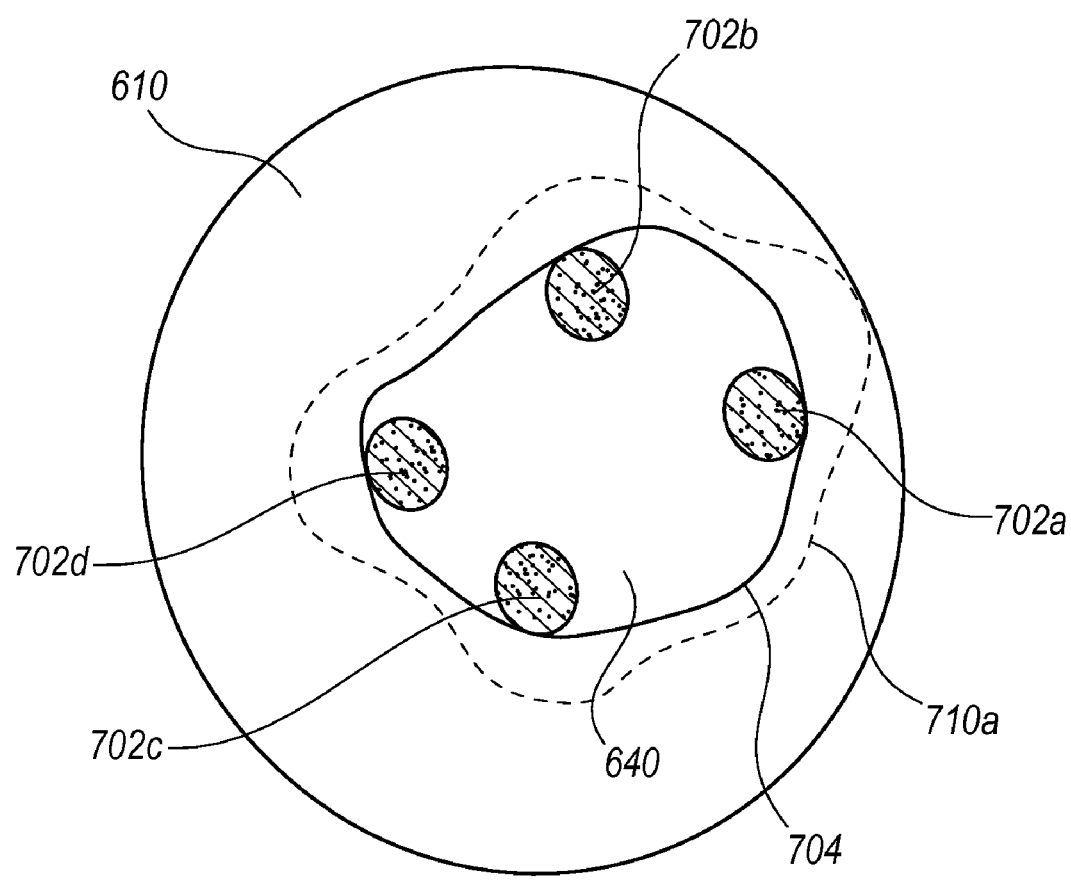
FIG. 41 shows a treatment penetrating the surrounding tissue using multiple localized treatment seeds.

FIG. 41 shows treatment penetrating tissue 610 including multiple localized treatment seeds 702a-702d. In contrast to the single-seed embodiment of FIG. 39, depth of penetration is somewhat uneven as the depths of radiation penetration into tissue 610 are more pronounced near each of seeds 702a-702d. Eventually the radioactive treatment ends due to the dying-off of radioactivity from seeds 702a-702d. However, where seeds 702a-702d are made from a lasting material, for example permanent site markers, seeds 702a-702d remain to be used for identification of target site 640 in the future.

Figure 42:
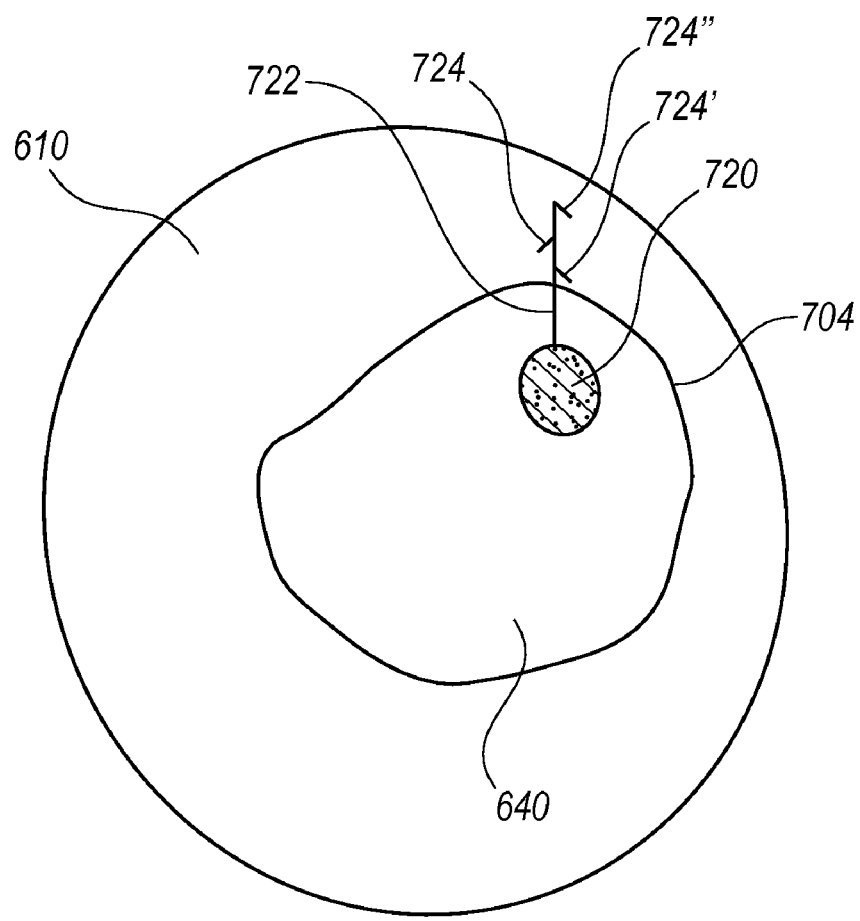
FIG. 42 shows a tissue anchor for a localized treatment seed within a patient.

FIG. 42 shows an anchored localized treatment seed 720 within a patient. Rather than a free-floating treatment seed (shown in the preceding embodiments with respect to FIGS. 39-41), seed 720 is anchored to the patient tissue 610 such that seed 720 can be placed in a specific location at target site 640 and may maintain that positioning to provide interstitial brachytherapy. Anchored seed 720 includes a shaft 722 projecting from the main body of seed 720 and includes barbs 724, 724', 724" that are placed along a shaft. When shaft 722 is plunged within tissue 610, barbs 724, 724', 724" prevent, or at least substantially reduce the possibility of, seed 720 moving location at target site 640. In this way, seed 720 may be advantageously placed at target site 640 to provide interstitial brachytherapy to a specific location at target site 640.

Moreover, multiple anchored seeds 720 may be positively located at the periphery of target site 640 to provide highly selective location of the therapy. Anchored seed 720 may be end-deployed from a cannula using a pushrod such as is described below in detail with respect to FIGS. 46 and 47. However, anchored seed 720 may also be deployed in a side-deployment configuration wherein the pushrod holds seed 720 for applying pressure against the interior wall of target site 640 for fixing attachment. In such a delivery embodiment, a pushrod may hold seed 720 with a predetermined mount of force and release seed 720 when pulled away. In this way, seed 720 would be held while plunging barbs 724 into tissue 640 and release once placed.

Referring now to FIGS. 43A-43B, cross-sections of a generally cylindrical seed 730 are shown. Seed 730 may be used for the brachytherapy methods disclosed herein and comprises a generally cylindrical body having radioactive particles or granules 732 held together in a binder 734. Granules 732 are typically chosen as rich in I-125 as a radioactive source in interstitial brachytherapy. However, other advantageous materials may be used for granules 732. Moreover, the size and number of granules 732 may be adjusted accordingly to provide a desirable dose of radiation. Binder 734 may be a polymeric binding substance or other substance that is generally impervious. In an alternative embodiment, binder 734 may be biosorbable allowing for granules 732 to be placed at target site 640 (described above) and then essentially released from binder 734 when binder 734 is absorbed by the body.

FIG. 43C shows a cross-section of a generally spherical seed 740 having granules 742. In contrast to the embodiment of FIGS. 43A-B, seed 740 is configured with granules 742 being generally evenly spaced apart within body 744. In so doing, the radiation pattern emanating from seed 740 is also evenly distributed.

FIG. 44 shows a caged seed 750. In this embodiment, a radioactive seed 88 is housed within a meshed body portion 752. Caged seed 750 may also used as a site marker for imaging under multiple modalities. Site markers and deployment devices are described in detail in U.S. patent application Ser. No. 11/242,334, filed Oct. 3, 2005, to Michael E. Miller, et al., entitled "Site Marker Visible Under Multiple Modalities," the contents of which are incorporated by reference in their entirety. Caged seed 80 may be constructed of a foam-like material. The foam-like material may be a carbon filled polymer or a glass filled polymer so as to be visible under multiple modalities. In addition, the foam-like material may contain therapeutic materials to deliver medication to the biopsy site. One exemplary material for construction of caged seed 750 is a thrombin filled polymer. The foam-like material acts as a matrix for tissue ingrowths.

FIG. 45 shows a caged seed 760 wherein a cage 752 includes barbs 768 such that the cage and seed do not move once deployed. An outside surface 764 of a meshed body portion 762 is provided with one or more barbs 768 disposed thereon. Barbs 768 assist in adhering therapeutic marker 760 to internal walls of the biopsy cavity such as target site 640 (described above). Barbs 768 are configured so as to extend at a predetermined angle relative to outside surface 764. In one specific embodiment, barbs 768 are configured to extend perpendicular to outside surface 764. In another embodiment, barbs 768 are positioned at different angles relative to one another, including opposing one another.

Figure 46:
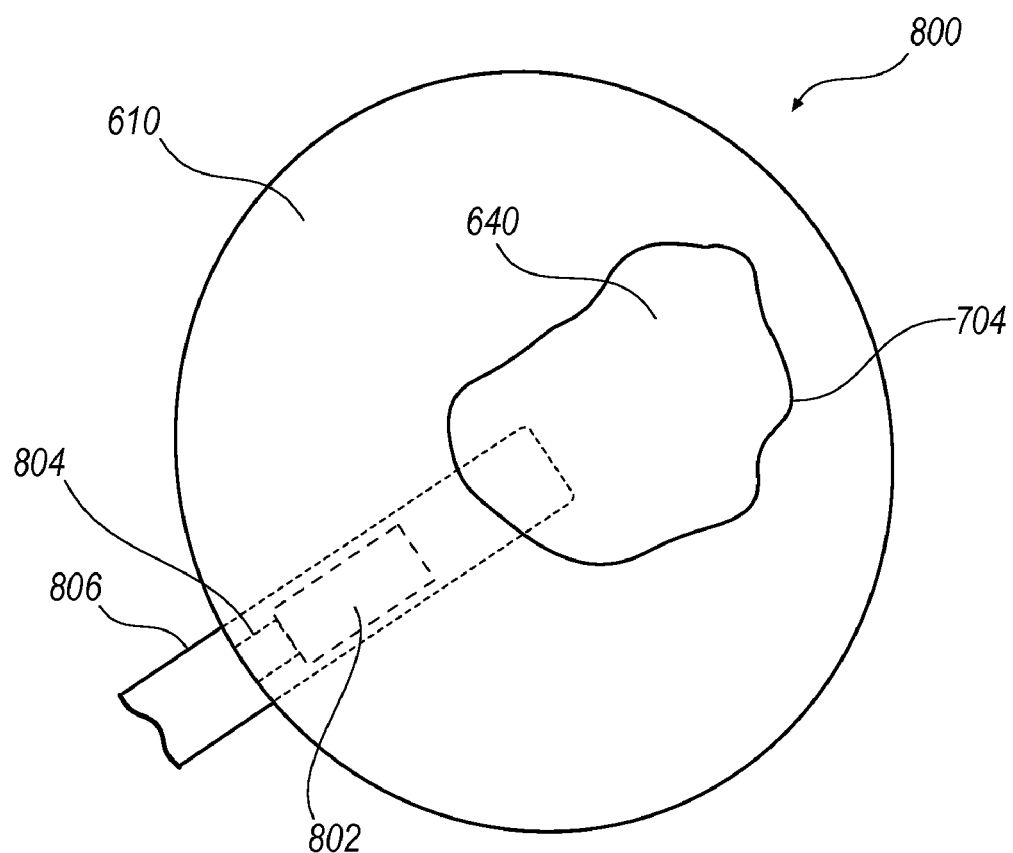
FIG. 46 shows a compressed foam capsule being delivered to the target site.

FIG. 46 shows a compressed foam treatment 802 being delivered to target site 640. Foam treatment 802 is delivered through a cannula 806 using a push rod 804 to push foam treatment 802 through cannula 806 to target site 640. As discussed in detail below with respect to FIGS. 47-48, foam treatment 802 is delivered in a compressed state and ultimately expands to substantially fill target site 640. Foam treatment 802 is a foam-based medium that is treated with a therapeutic substance. The therapeutic substance may be a powdered radioactive material or a coating of radioactive material for providing interstitial brachytherapy. However, the therapeutic material may also be a drug, or a combination of a drug and a radioactive material.

Figure 48:
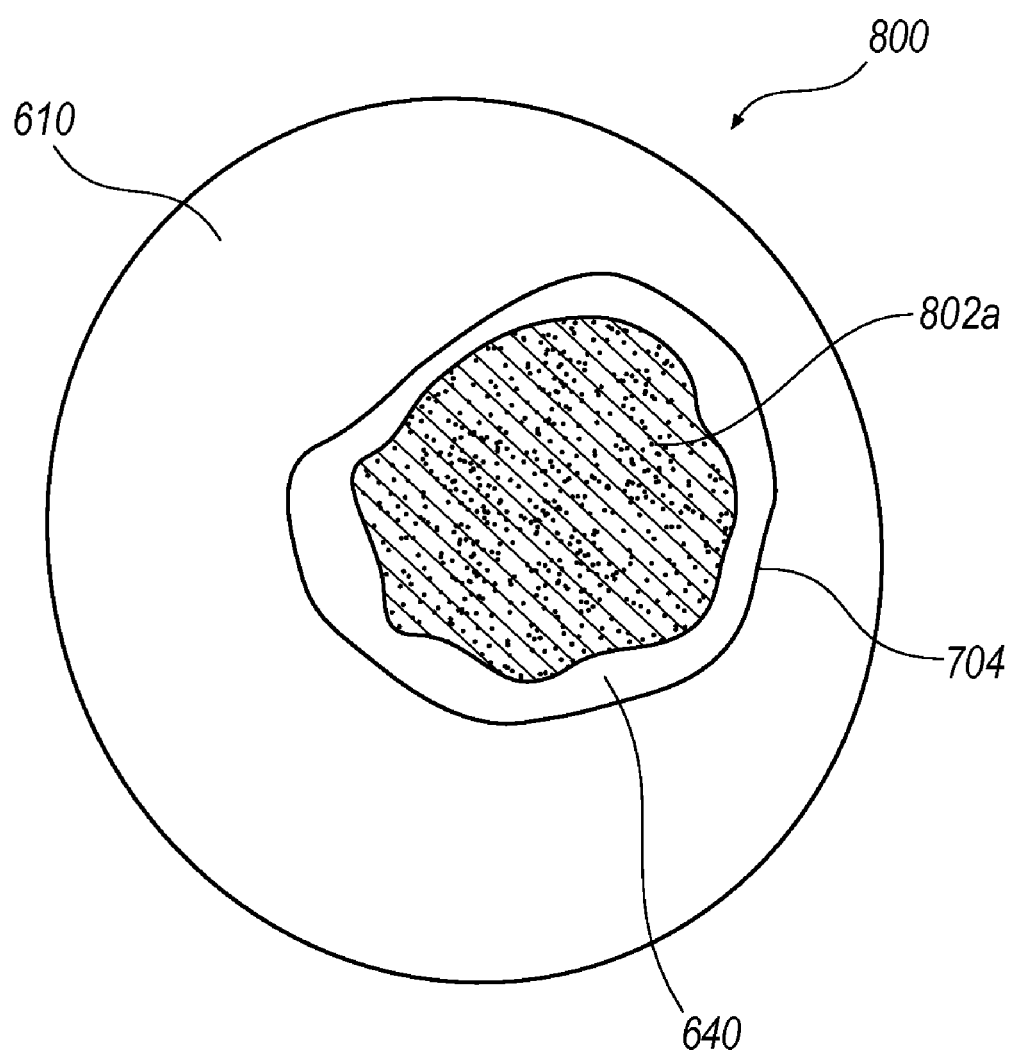
FIG. 48 shows an expanded foam capsule substantially filling the target site.

The foam-based medium is a biosorbable material, for example, collagen based or a polyglycolic acid. Once delivered to target site 640, the biosorbable material slowly dissolves and is absorbed by the body. Moreover, the material absorbs moisture from the body in order to expand to a larger volume (as shown in FIG. 48). In an alternative embodiment, the foam material may be a non-biosorbable material that is compatible for permanent placement in the body.

Figure 47:
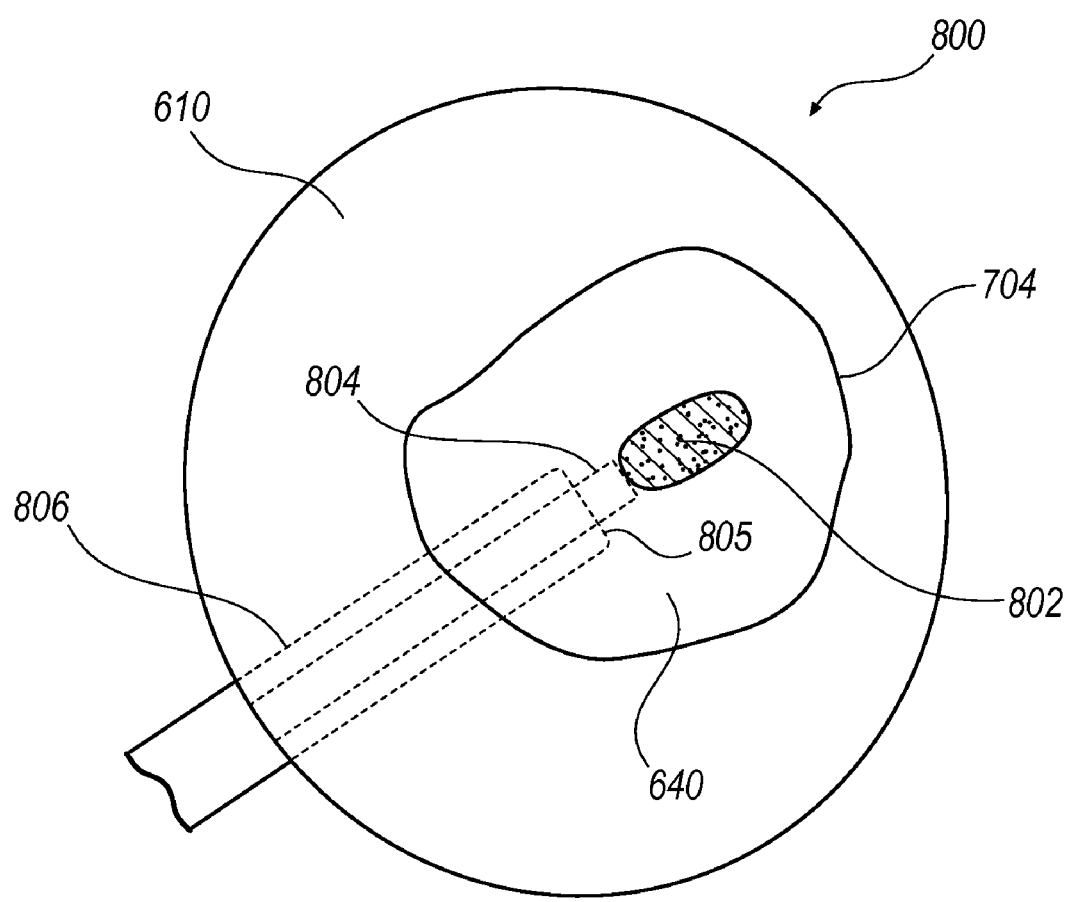
FIG. 47 shows a delivered foam capsule at the target site.

FIG. 47 shows foam treatment 802 at target site 640. Once pushrod 804 is extended beyond a distal end 805 of cannula 806, foam treatment 802 is delivered to target site 640 which is typically a cavity created by resecting tissue. Foam treatment 802, and the therapeutic agent, may now react with the tissue surrounding target site 640.

FIG. 48 shows an expanded foam treatment 802a in an expanded state and substantially filling target site 640. The nature of the foam-like material of foam treatment 802a may expand naturally, may be triggered for expansion by body heat, may react with moisture at target site 640, or may absorb moisture at target site 640 to expand. Foam treatment 802a expands to fill a larger volume than when in the delivery state shown in FIGS. 46-47. As shown in FIG. 48, foam treatment 802a substantially fills the volume of target site 640. In an alternative embodiment, foam treatment 802a may expand to fill target site 640 entirely such that foam treatment enlarges target site 640 (e.g., pushes against the walls of target site 640) and is in pressing contact with the interior surface of target site 640 to provide treatment that requires contact with tissue. In the expanded state, foam treatment 802a is also visible under multiple imaging modalities to ensure proper placement, expansion, and later location of target site 640. Although the foam-like material may be biosorbable, for at least a time the foam-like substance remains and is identifiable using multiple imaging modalities.

Figure 49:
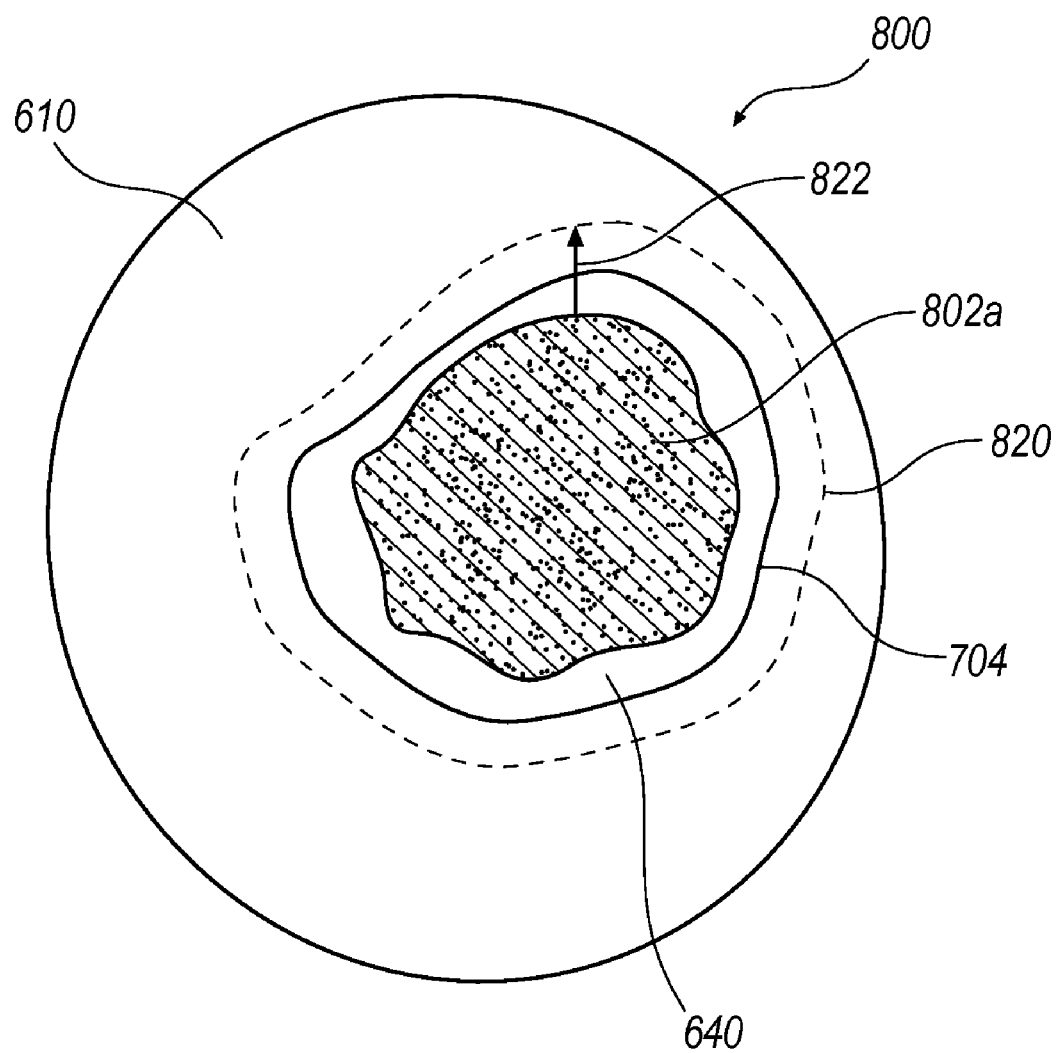
FIG. 49 shows a treatment penetrating the surrounding tissue using an expanded foam delivery mechanism.

FIG. 49 shows treatment penetrating the surrounding tissue of target site 640 where foam treatment 802a is in an expanded configuration. The treatment penetrates to a depth 822 of the surrounding tissue in a substantially uniform manner. In an embodiment, the treatment penetration is radiation from radioactive materials coated or infused to foam treatment 802a. In another embodiment, the treatment penetration is due to a pharmaceutical or drug penetration delivered by foam treatment 802a. In yet another embodiment, the treatment penetration is both a radiation and a pharmaceutical. Because foam treatment 802a substantially fills target site 640, the treatment is generally uniform in the tissue in contrast to the less uniform treatment distribution using multiple seeds 702a-702d of FIG. 40.

Figure 50:
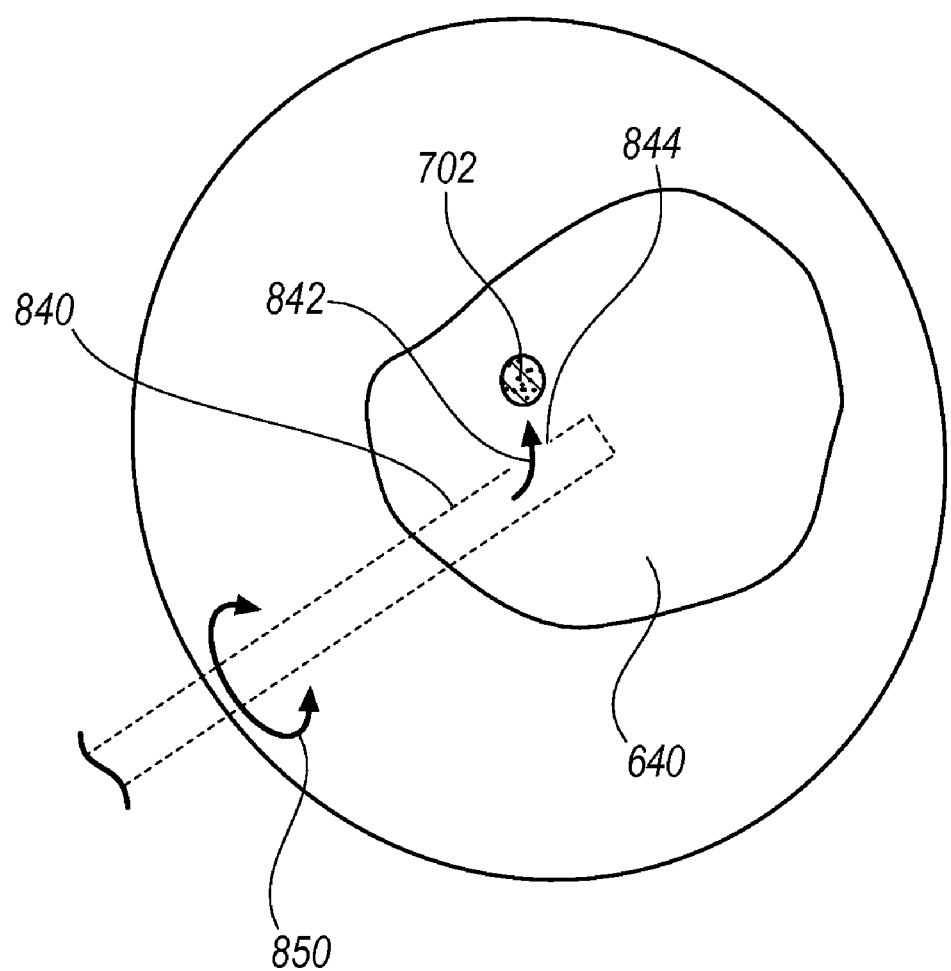
FIG. 50 shows the deployment and placement of treatment seeds around the debulked area.

FIG. 50 shows a deployment device 840 and placement of a treatment seed at the debulked target site 640. In contrast to the end-deployment of FIGS. 46 and 47, deployment of seed 702 is performed in this embodiment through a side port 844. A pushrod (not shown) may deploy 842 down the cannula of deployment device 840 and out port 844. Deployment methods, apparatuses, and others, are described in detail in U.S. patent application Ser. No. 11/305,141, filed Dec. 16, 2005, to Terry D. Hardin, et al., entitled "Biopsy Site Marker Deployment Device," the contents of which are incorporated by reference in their entirety.

Side port 844 may be selectively rotated 850 to provide an orientation relative to the inner periphery of target site 640 for targeted deployment. That is, as shown in FIG. 50, seed 720 is deployed generally to the top portion of target site 640. However, a user may rotate 850 deployment device 840 such that side port 844 would deploy seed 702 to the bottom portion of target site 640. In this way, the user may selectively position side port 844 for the deployment of seeds 702 in target site 640.

Figure 51:
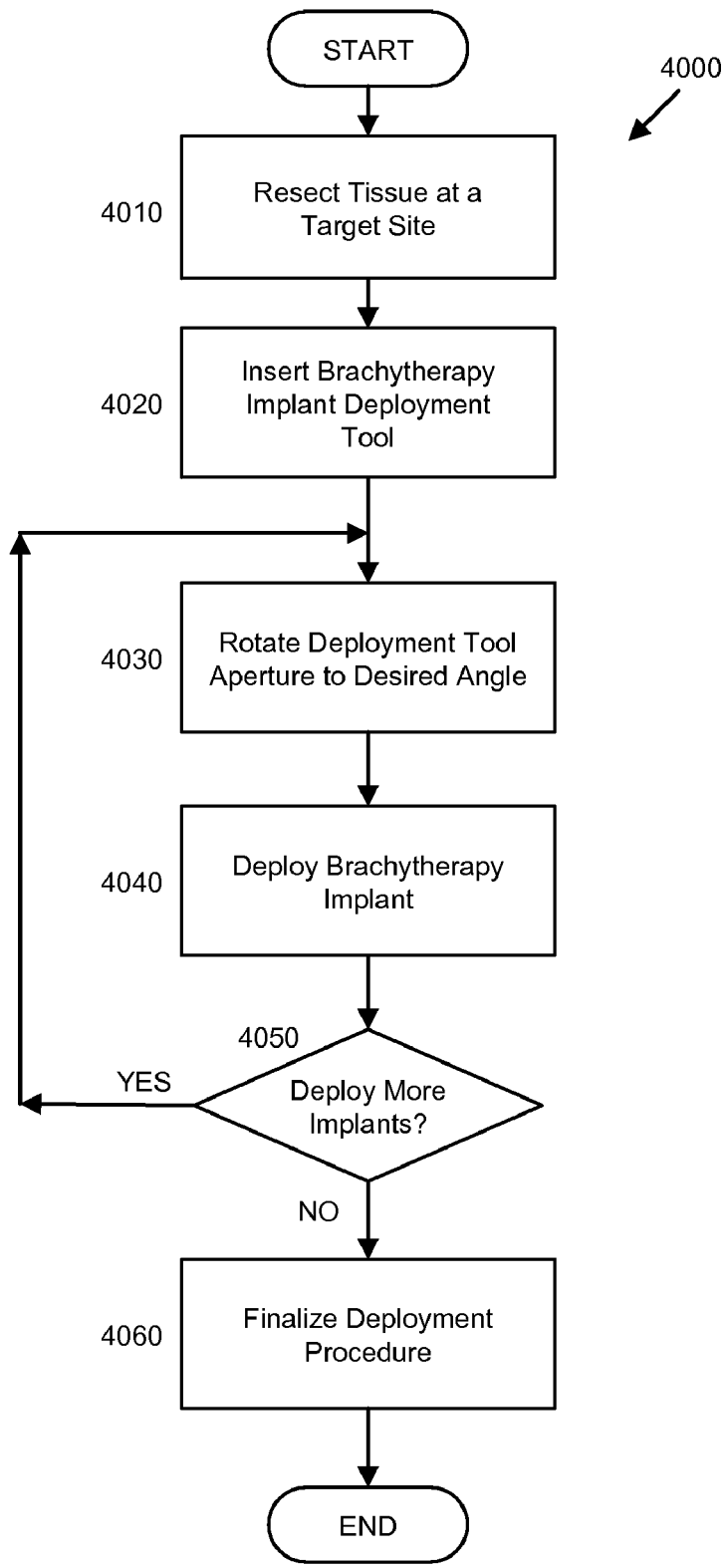
FIG. 51 shows a flow diagram of deployment and placement of one or multiple treatment seeds at the debulked area.

FIG. 51 shows a flow diagram of deployment and placement method 4000 of one or multiple treatment seeds 702, and other treatment mechanisms described herein, at the debulked target site 640. Deployment and placement method 4000 in general provides that a cavity is created and brachytherapy implants (e.g., seeds 702, and foam 802) are placed within target site 640 at a desired location. Deployment and placement method 4000 begins at step 4010 where tissue is resected from target site 640. In this step, tissue is debulked in gross to remove, for example, suspected cancerous tissue. Other adjuvant therapies, such as those described herein, may be used once resection is complete. Moreover, methods of testing for removal of a margin may also be used, such as the inking method described herein. Once debulking and adjuvant therapy are complete, control proceeds to step 4020.

At step 4020, a brachytherapy deployment tool is inserted to target site 640. In some instances, such as where end-deployment is preferred, the outer cannula of the resection device may be used as a deployment tool. (See FIGS. 46 and 47). Alternatively, the introducer cannula used for the resection device may be used for end-deployment. Otherwise, a side-deployment tool (see FIG. 50) may be inserted in preparation of deployment of a brachytherapy seed or foam. Once the deployment tool is inserted, control proceeds to step 4030.

At step 4030, rotation of the deployment tool is performed such that the deployment opening (see side port 844 of FIG. 50) is positioned in a location for deployment. The positioning of the deployment opening will determine where the brachytherapy seed (e.g., seed 702) will be positioned once deployed. Thus, the side opening is rotated to align with the intended location of delivery. Rotation of the deployment tool is not required or preferred when end-deployment is used.

Where multiple brachytherapy seeds are deployed (see step 4050 below), rotation is preferred at least such that brachytherapy seeds are deployed at different positions within target site 640. For example, where four seeds are to be deployed (see FIG. 41 above), then the deployment tool should be rotated ninety degrees (90°) with the deployment of each seed to position the seeds spacedly within target site 640. Additionally, when a barbed device for maintaining position within cavity 640 is used (see caged seed 760 FIG. 45 above) the deployment opening (see side port 844 of FIG. 50) is of importance because the orientation of the opening will control where the seed is deposited and will substantially remain in that position. Control then proceeds to step 4040.

At step 4040, the brachytherapy implant is deployed. For example, a pushrod is moved distally through the deployment device to push the brachytherapy implant distally for end or side deployment. Control proceeds to step 4050.

At step 4050, the user determines whether or not to deploy more (or multiple) implants. For example, a single seed 702 is deployed in FIG. 38. Alternatively, multiple seeds 702a-702d are shown deployed in FIG. 40. Moreover, where a foam-type brachytherapy delivery is used, only a single foam treatment 802 is deployed (see FIGS. 46 and 47). However, where treatment site 640 is a large cavity (e.g., having a large volume), multiple foam treatments 802 may be deployed to fill the cavity if a single foam treatment 802 would not sufficiently fill the volume when expanded. If the user decides more implants should be deployed, control proceeds to step 4030. If no more implants are desired to be deployed, control proceeds to step 4060.

At step 4060, the deployment procedure is finalized by removing the deployment device from the patient. Deployment and placement method 4000 then ends.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A method of establishing a margin region comprising:
   forming a cavity by resecting tissue, said cavity having an inner wall of tissue at a desired biopsy location;
   applying ink to at least a portion of said inner wall of said cavity subsequent to forming said cavity, said ink penetrating said tissue to form an inked tissue region at least partially defined by said inner wall and an inked tissue boundary located a distance from said inner wall, said inked tissue boundary separating said inked tissue from non-inked tissue;
   removing a tissue sample comprising at least a portion of said inked tissue boundary, and at least a portion of said inked and non-inked tissue; and
   determining a pathology of said inked portion of said tissue sample.

2. The method of claim 1, wherein said determining a pathology comprises testing said inked tissue for cancerous material.

3. The method of claim 1, further comprising:
   repeating applying ink to at least a portion of said inner wall of said cavity to form an inked tissue region having an inked tissue boundary, removing a tissue sample comprising at least a portion of said inked tissue boundary, and determining a pathology of an inked portion of said tissue sample, when the pathology of a previous tissue sample indicates diseased tissue is present within said inked portion of said previous tissue sample.

4. The method of claim 1, wherein said determining a pathology comprises determining whether said inked portion of said tissue sample is clear of diseased material.

5. The method of claim 1, further comprising:
   administering an adjuvant treatment.

6. The method of claim 5, wherein said adjuvant treatment is selected from one of: resecting tissue, ablating tissue, heating tissue, freezing tissue, applying chemicals to tissue, external beam HIFU therapy, interstitial HIFU therapy, electroporation therapy, ultrasonicporation therapy, interstitial microwave therapy, and brachytherapy.

7. The method of claim 5, further comprising:
   inserting an adjuvant therapy device into said cavity; and
   applying a vacuum within said cavity while administering said adjuvant treatment, said vacuum causing said cavity to collapse around said adjuvant treatment device.

8. The method of claim 5, further comprising administering a haemostatic agent to said inner wall prior to administering said adjuvant treatment.

9. The method of claim 5, further comprising administering said adjuvant treatment before applying said ink to said inner wall.

10. The method of claim 5, further comprising administering said adjuvant treatment to said inner wall of said cavity before applying said ink to said inner wall.

11. The method of claim 1, further comprising:
    administering a haemostatic agent to said cavity before applying said ink to said inner wall.

12. The method of claim 11, further comprising administering an adjuvant treatment to said inner wall of said cavity after administering said haemostatic agent to said cavity and before applying said ink to said inner wall.

13. The method of claim 1, further comprising locating an inked portion of said tissue sample determined to have been located nearest to said cavity for testing.

14. The method of claim 13, wherein determining a pathology comprises testing said portion of said inked tissue sample determined to have been located nearest to said cavity.

15. The method of claim 1, further comprising removing a second tissue sample and determining the presence of inked tissue in said second tissue sample, and repeating said step of removing said tissue sample when the second tissue sample is determined to have inked tissue.

16. A treatment method for improving an adjuvant therapy comprising:
   resecting tissue to form a cavity having surrounding tissue and an inner wall;
   applying a haemostatic agent to said surrounding tissue;
   applying an adjuvant therapy by an adjuvant therapy device to said surrounding tissue following application of said haemostatic agent;
   applying ink to at least a portion of said inner wall of said cavity following application of said adjuvant therapy, said ink penetrating said tissue to create an inked tissue region at least partially defined by said inner wall and an inked tissue boundary located a distance from said inner wall, said inked tissue boundary separating said inked tissue from non-inked tissue;
   resecting a tissue sample from said surrounding tissue after said applying said adjuvant therapy, said tissue sample including at least a portion of said inked tissue boundary, and at least a portion of said inked and non-inked tissue; and
   determining whether said inked portion of said tissue sample is clear of diseased material.

17. The method of claim 16, further comprising:
   continuing to resect tissue to form a larger cavity if said inked tissue is determined as not clear of diseased material.

18. The method of claim 17, further comprising repeating applying said haemostatic agent, applying said adjuvant therapy, applying said ink to said inner wall, and resecting a tissue sample, when said determining a pathology indicates cancerous material is present within said inked portion of said tissue sample.

19. The method of claim 16, wherein the adjuvant therapy is selected from one of: resecting tissue, ablating tissue, heating tissue, freezing tissue, applying chemicals to tissue, external beam HIFU therapy, interstitial HIFU therapy, electroporation therapy, ultrasonicporation therapy, interstitial microwave therapy, and brachytherapy.

* * * * *